(12) United States Patent
Ikemoto et al.

(10) Patent No.: US 7,468,448 B2
(45) Date of Patent: Dec. 23, 2008

(54) PRODUCTION METHOD OF HEXAHYDROFUROFURANOL DERIVATIVE, INTERMEDIATE THEREFOR AND PRODUCTION METHOD THEREOF

(75) Inventors: Tetsuya Ikemoto, Osaka (JP); Dongguo Piao, Sapporo (JP)

(73) Assignee: Sumitomo Chemical Company, Ltd., Tokyo (JP)

( * ) Notice: Subject to any disclaimer, the term of this patent is extended or adjusted under 35 U.S.C. 154(b) by 220 days.

(21) Appl. No.: 11/064,573

(22) Filed: Feb. 24, 2005

(65) Prior Publication Data

US 2005/0256322 A1    Nov. 17, 2005

Related U.S. Application Data

(63) Continuation-in-part of application No. 10/744,733, filed on Dec. 23, 2003, now Pat. No. 6,867,321.

(30) Foreign Application Priority Data

Dec. 27, 2002   (JP)   ............................. 382584/2002
Jun. 16, 2003   (JP)   ............................. 171303/2003

(51) Int. Cl.
    *C07D 493/06*   (2006.01)
(52) U.S. Cl. ...................................... 549/464
(58) Field of Classification Search .................. 549/464
    See application file for complete search history.

(56) References Cited

U.S. PATENT DOCUMENTS

| 5,399,722 | A  | 3/1995 | Beck et al.    |
| 6,867,321 | B2 | 3/2005 | Ikemoto et al. |
| 2004/0127727 | A1 | 7/2004 | Ghosh et al. |

FOREIGN PATENT DOCUMENTS

| EP | 0 539 192 A1    | 4/1993  |
| WO | WO 99/67254 A2  | 12/1999 |
| WO | WO 01/25240 A1  | 4/2001  |
| WO | WO 2004/002975 A1 | 1/2004 |

OTHER PUBLICATIONS

Evans et al., *J. Am. Chem. Soc.*, 121(4): 669-685 (1999).
Fráter et al., *Tetrahedron*, 40(8): 1269-1277 (1984).
Ghosh et al., *Tetrahedron Letters*, 36(4): 505-508 (1995).
Kitamura et al., *Tetrahedron: Asymmetry*, 1(1): 1-4 (1990).
Pezechk et al., *Tetrahedron Letters*, 27(32): 3715-3718 (1986).
Uchiyama et al., *Tetrahedron Letters*, 42: 4653-4656 (2001).
Yamada et al., *Heterocycles*, 26(11): 2841-2844 (1987).

*Primary Examiner*—Taofiq A Solola
(74) *Attorney, Agent, or Firm*—Leydig, Voit & Mayer, Ltd.

(57) ABSTRACT

The present invention provides a method for producing compound (XIV) useful as an intermediate for pharmaceutical agents efficiently and economically on an industrial scale without using ozone oxidation and highly toxic reagent, and an intermediate used for this method. Particularly, the present invention provides a method for producing a compound having an absolute configuration represented by the formula (XV) and an enantiomer thereof without using a technique such as optical resolution and the like, and an intermediate used for this method.

(1) Compound (XIII) as a starting material is led to compound (I), and after introducing a protecting group, subjected to reduction and cyclization to give compound (XIV). Particularly, compound (XIII) as a material is led to compound (I) via compound (XX) to produce compound (XIV). Using an optically active compound (XIII) as a starting material, a compound having an absolute configuration represented by the formula (XV) and the like are produced highly stereoselectively.

(2) Compound (XXI) as a starting material is stereoselectively reduced to give compound (XXII), and by introduction of a protecting group, reduction and cyclization, compound (XXVI) is obtained, and by inverting hydroxyl group, compound (XV) is produced.

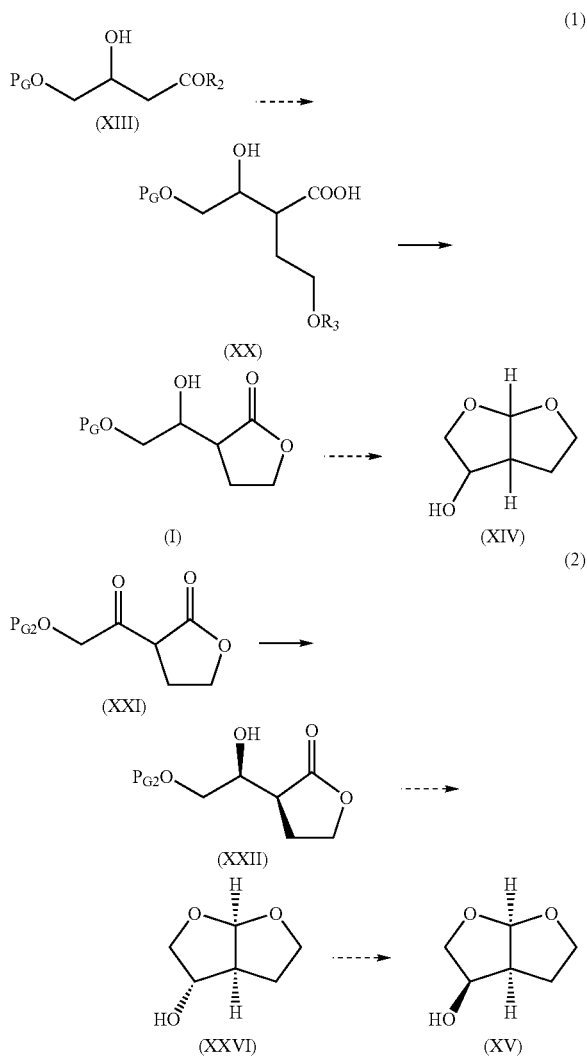

wherein each symbol is as defined in the specification.

18 Claims, No Drawings

PRODUCTION METHOD OF HEXAHYDROFUROFURANOL DERIVATIVE, INTERMEDIATE THEREFOR AND PRODUCTION METHOD THEREOF

CROSS-REFERENCE TO RELATED APPLICATION

This patent application is a continuation-in-part of U.S. patent application Ser. No. 10/744,733, filed Dec. 23, 2003, now U.S. Pat. No. 6,867,321.

TECHNICAL FIELD OF THE INVENTION

The present invention relates to a hexahydrofurofuranol derivative represented by the formula (XIV), particularly the formula (XV), provided below, which is an intermediate for a pharmaceutical product, compounds represented by the formulas (A), (B) and (C), provided below, which are useful as synthetic intermediates therefor and production methods thereof.

BACKGROUND OF THE INVENTION

A compound represented by the formula (XIV):

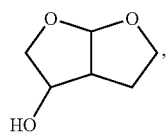

(XIV)

particularly the formula (XV):

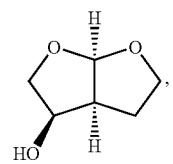

(XV)

is a compound useful as an intermediate for an anti-AIDS drug (International Publication No. 01/25240 and International Publication No. 99/67254). Methods for synthesizing a compound represented by the formula (XIV) or (XV) are described in International Publication No. 01/25240, EP-A-539192, Tetrahedron Letters, 27, p. 3715 (1986) and Tetrahedron Letters, 4, p. 505 (1995). However, they use ozone oxidation and tributyltin hydride etc. having high toxicity, and are not industrially preferable methods. Of the abovementioned references, International Publication No. 01/25240, EP-A-539192 and Tetrahedron Letters, 4, p. 505 (1995) comprise optical resolution of the obtained racemate with an enzyme and the like to give an optically active compound, whose relative configuration is represented by the formula (XV), and are inefficient. Recently, a method for directly synthesizing an optically active compound having the relative configuration is represented by the formula (XV), has been reported in Tetrahedron Letters, 42, p. 4653 (2001). This method uses an organic selenium compound having high toxicity, and is not entirely applicable to industrial use.

SUMMARY OF THE INVENTION

An object of the present invention is to provide a method for producing a compound represented by the formula (XIV) (hereinafter to be also referred to as compound (XIV)), which is useful as an intermediate for an anti-AIDS drug, efficiently and economically on an industrial scale by resolving the problems of conventional production methods, such as ozone oxidation and use of highly toxic reagents, an intermediate used for the method and a production method thereof, particularly, a method for producing compound (XIV) having an absolute configuration represented by the formula (XV) and an enantiomer thereof, without using a technique such as optical resolution and the like, an intermediate for the method and a production method thereof.

The present invention comprises a method for producing the compound (XIV), which comprises using a compound represented by the formula (XIII):

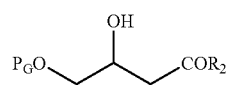

(XIII)

wherein $P_G$ is a hydroxy-protecting group, and $R_2$ is a lower alkoxyl group or a lower alkylthio group, used as a starting material, to form a compound represented by the formula (I):

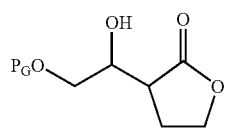

(I)

wherein $P_G$ is as defined above, introducing a protecting group, followed by reduction and cyclization to form compound (XIV), and novel compounds represented by the formulas (A) and (B) provided below, which are intermediates for the method. Moreover, the present invention comprises a method for producing compound (XIV), which comprises using a compound represented by the formula (XIII) as a starting material to form a compound represented by the formula (XIX):

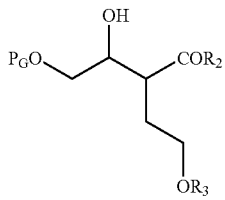

(XIX)

wherein $P_G$ and $R_2$ are as defined above, and $R_3$ is a hydroxy-protecting group or a hydrogen atom, hydrolyzing the compound to give a compound represented by the formula (XX):

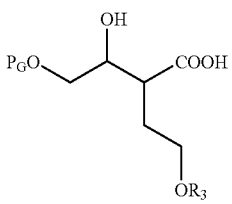

(XX)

wherein $P_G$ and $R_3$ are as defined above, which is then processed to form a compound represented by the formula (I) or the formula (III):

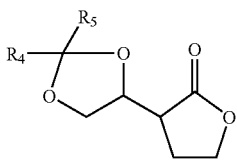

(III)

wherein $R_4$ and $R_5$ are the same or different and each is independently a hydrogen atom, a lower alkyl group, a lower alkoxyl group or a phenyl group, or $R_4$ and $R_5$ are optionally taken together to form an α,ω-alkylene group having 2 to 5 carbon atoms, wherein one of the carbon atoms at positions other than α-position and ω-position is optionally substituted by an oxygen atom or a sulfur atom, which is an intermediate for the aforementioned method, as well as a novel compound represented by the formula (C) presented below, which is an intermediate for the method.

According to the method of the present invention, compound (XIV) can be produced efficiently and economically on an industrial scale without using highly toxic reagents or ozone oxidation. Moreover, the present invention comprises a method wherein a compound represented by the formula (XIII) can be used to form a compound whose absolute configuration is represented by the formula (VII):

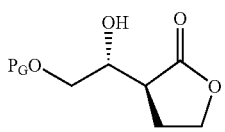

(VII)

wherein $P_G$ is as defined above, or an enantiomer thereof, highly stereoselectively at a superior optical purity, using an optically active form of the formula (XIII), particularly an optically active form having a high optical purity, as a starting material according to the above-mentioned method, without using techniques such as optical resolution and the like. The optically active form of the compound represented by the formula (III) can be produced economically on an industrial scale using a BINAP catalyst or a biological catalyst (U.S. Pat. No. 5,399,722, Heterocycles, 26, 2841 (1987)), and that a compound whose absolute configuration is represented by the formula (VII) or an enantiomer thereof can be stereoselectively converted at a superior optical purity to a compound whose absolute configuration is represented by the formula (XV) or an enantiomer thereof.

A method of the present invention proceeds via the carboxylic acid represented by the aforementioned formula (XX), a compound whose absolute configuration is a compound represented by the formula (XVIII):

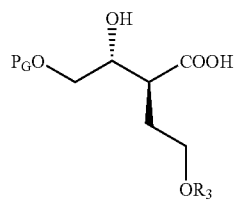

(XVIII)

wherein $P_G$ and $R_3$ are as defined above, or an enantiomer thereof can be obtained highly stereoselectively at a superior optical purity by applying purification when going through said carboxylic acid, thereby increasing the diastereomer purity, and that a compound having an absolute configuration represented by the formula (XVIII) or an enantiomer thereof can be converted highly stereoselectively at a superior optical purity to a compound whose absolute configuration is represented by the formula (XV) or an enantiomer thereof.

Since the present invention does not use ozone oxidation or a highly toxic reagent, it is a useful method for producing an optically active form, as well as a superior method for producing a racemate as compared to conventional methods.

The present invention further comprises a method for producing a compound having a relative configuration represented by the formula (XV) by stereoselectively reducing a compound represented by the formula (XXI):

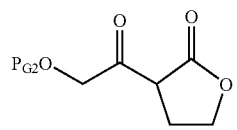

(XXI)

wherein $P_{G2}$ is a hydroxy-protecting group (hereinafter to be also referred to as compound (XXI)) to form a compound having a relative configuration represented by the formula (XXII):

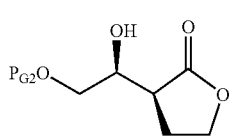

(XXII)

wherein $P_{G2}$ is as defined above, introducing a protecting group, reducing and cyclizing the compound to form a compound having a relative configuration represented by the formula (XXVI):

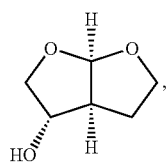

(XXVI)

and inverting a hydroxyl group to form a compound having a relative configuration represented by the formula (XV), and novel compounds having relative configurations represented by the formulas (G) and (H) presented below.

According to the method of the present invention, a compound having a relative configuration represented by the formula (XV), particularly, a compound having an absolute configuration represented by the formula (XV) and an enantiomer thereof can be produced efficiently and economically on an industrial scale without using a highly toxic reagent or ozone oxidation.

Accordingly, the present invention provides the following.

(1) A compound represented by the formula (A):

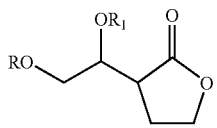

(A)

wherein R and $R_1$ are the same or different and each is independently a hydroxy-protecting group or a hydrogen atom, or taken together to represent a group of the formula:

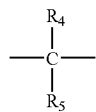

wherein $R_4$ and $R_5$ are the same or different and each is independently a hydrogen atom, a lower alkyl group, a lower alkoxyl group or a phenyl group, or $R_4$ and $R_5$ are optionally taken together to form an α,ω-alkylene group having 2 to 5 carbon atoms, wherein one of the carbon atoms at positions other than α-position and ω-position is optionally substituted by an oxygen atom or a sulfur atom, provided that when $R_1$ is a hydrogen atom, R is a hydroxy-protecting group, and a relative configuration of the compound of the formula (A) is syn, then is R should be a hydroxy-protecting group other than benzyl group.

(2) The compound of the above-mentioned (1), wherein $R_4$ and $R_5$ are the same or different and each is independently a hydrogen atom, a lower alkyl group, a lower alkoxyl group or a phenyl group.

(3) A compound represented by the formula (B):

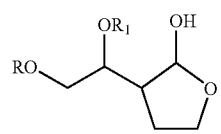

(B)

wherein R and $R_1$ are the same or different and each is independently a hydroxy-protecting group or a hydrogen atom, or taken together to represent a group of the formula:

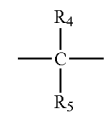

wherein $R_4$ and $R_5$ are the same or different and each is independently a hydrogen atom, a lower alkyl group, a lower alkoxyl group or a phenyl group, or $R_4$ and $R_5$ are optionally taken together to form an α,ω-alkylene group having 2 to 5 carbon atoms, wherein one of the carbon atoms at positions other than α-position and ω-position is optionally substituted by an oxygen atom or a sulfur atom.

(4) The compound of (3), wherein $R_4$ and $R_5$ are the same or different and each is independently a hydrogen atom, a lower alkyl group, a lower alkoxyl group or a phenyl group.

(5) The compound of (1), which has a relative configuration represented by the formula (D):

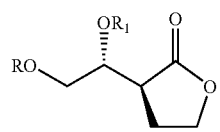

(D)

wherein R and $R_1$ are as defined in (1)

(6) The compound of (3), which has a relative configuration represented by the formula (E):

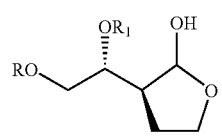

(E)

wherein R and $R_1$ are as defined in the above-mentioned (3).

(7) The compound of (1), which has an absolute configuration represented by the formula (D), or an enantiomer thereof.

(8) The compound of (3), which has an absolute configuration represented by the formula (E), or an enantiomer thereof.

(9) The compound of (1), (5) or (7), wherein $R_1$ is a hydrogen atom and R is a t-butyl group.

(10) The compound of any of (1), (3), (5), (6), (7) and (8), wherein R and $R_1$ are taken together to represent a group of the formula:

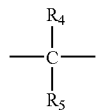

wherein $R_4$ and $R_5$ are methyl groups, or $R_4$ and $R_5$ are optionally taken together to form an $\alpha,\omega$-alkylene group having 2 to 5 carbon atoms, wherein one of the carbon atoms at positions other than $\alpha$-position and $\omega$-position is optionally substituted by an oxygen atom or a sulfur atom.

(11) The compound of any of (1) to (8), wherein R is a benzyl group or a t-butyl group and $R_1$ is a 1-ethoxyethyl group or a 3,4,5,6-tetrahydro-2H-pyran-2-yl group.

(12) The compound of (5) or (7), wherein $R_1$ is a hydrogen atom and R is a benzyl group.

(13) A compound represented by the formula (C):

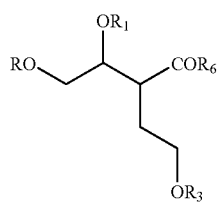

(C)

wherein R, $R_1$ and $R_3$ are the same or different and each is independently a hydroxy-protecting group or a hydrogen atom and $R_6$ is a hydroxyl group, a lower alkoxyl group or a lower alkylthio group, or a salt thereof.

(14) The compound of (13), which has an absolute configuration represented by the formula (F):

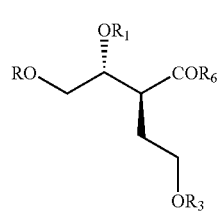

(F)

wherein R, $R_1$, $R_3$ and $R_6$ are as defined in (13), or an enantiomer thereof.

(15) The compound of (13) or (14), wherein R is a benzyl group, $R_1$ is a hydrogen atom, $R_3$ is a benzyl group or a t-butyl group, and $R_6$ is a hydroxyl group or an ethoxy group.

(16) A compound whose relative configuration is represented by the formula (G):

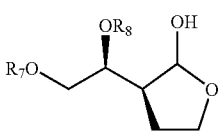

(G)

wherein $R_7$ and $R_8$ are the same or different and each is independently a hydroxy-protecting group or a hydrogen atom, or taken together to represent a group represented by the formula:

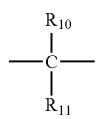

wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an $\alpha,\omega$-alkylene group having 2 to 5 carbon atoms, wherein one of the carbon atoms at positions other than $\alpha$-position and $\omega$-position is optionally substituted by an oxygen atom or a sulfur atom, provided that when $R_8$ is a hydrogen atom, and $R_7$ is a hydroxy-protecting group, then $R_7$ should be a hydroxy-protecting group other than a benzyl group.

(17) The compound of (16), wherein $R_{10}$ and $R_{11}$ are the same or different and each is independently a hydrogen atom, a lower alkyl group, a lower alkoxyl group or a phenyl group.

(18) A compound whose relative configuration is represented by the formula (H):

(H)

wherein $R_7$ and $R_8$ are the same or different and each is independently a hydroxy-protecting group or a hydrogen atom, or taken together to represent a group represented by the formula:

wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an $\alpha,\omega$-alkylene group having 2 to 5 carbon atoms, wherein one of the carbon atoms at positions other than α-position and ω-position is optionally substituted by an oxygen atom or a sulfur atom.

(19) The compound of (18), wherein $R_{10}$ and $R_{11}$ are the same or different and each is independently a hydrogen atom, a lower alkyl group, a lower alkoxyl group or a phenyl group.

(20) The compound of (16), which has an absolute configuration represented by the formula (G), or an enantiomer thereof.

(21) The compound of (18), which has an absolute configuration represented by the formula (H), or an enantiomer thereof.

(22) A method for producing a compound represented by the formula (I), which comprises hydroxyethylation of a compound represented by the formula (XIII), followed by cyclization.

(23) The method of (22), wherein the compound represented by the formula (I) has a relative configuration represented by the formula (VII).

(24) The method of (22) or (23), wherein the compound represented by the formula (XIII) is in an optically active form.

(25) The method of (22), wherein the compound represented by the formula (XIII) is a compound represented by the formula (XVI):

(XVI)

wherein each symbol is as defined in (22), and the compound represented by the formula (I) is a compound having an absolute configuration represented by the formula (VII), or the compound represented by the formula (XIII) is a compound represented by the formula:

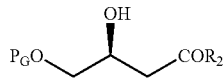

wherein each symbol is as defined in (22), and the compound represented by the formula (I) is an enantiomer of the compound having an absolute configuration represented by the is formula (VII).

(26) The method of (22), which comprises hydroxyethylating a compound represented by the formula (XIII) to form a compound represented by the formula (XIX), hydrolyzing the obtained compound represented by the formula (XIX) to form a compound represented by the formula (XX), and cyclizing the obtained compound represented by the formula (XX) to form the compound represented by the formula (I).

(27) The method of (26), wherein the compound represented by the formula (XIII) is a compound represented by the formula (XVI), the compound represented by the formula (XIX) is a compound having an absolute configuration represented by the formula (XVII):

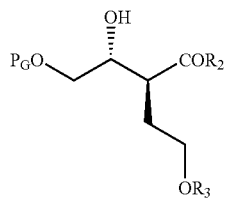

(XVII)

wherein each symbol is as defined in (26), the compound represented by the formula (XX) is a compound having an absolute configuration represented by the formula (XVIII), and the compound represented by the formula (I) is a compound having an absolute configuration represented by the formula (VII), or the compound represented by the formula (XIII) is an enantiomer of the compound represented by the formula (XVI), the compound represented by the formula (XIX) is an enantiomer of the compound having an absolute configuration represented by the formula (XVII), the compound represented by the formula (XX) is an enantiomer of the compound having an absolute configuration represented by the formula (XVIII), and the compound represented by the formula (I) is an enantiomer of the compound having an absolute configuration represented by the formula (VII).

(28) A method for producing a compound represented by the formula (III), which comprises the use of a compound represented by the formula (I).

(29) The method of (28), wherein $R_4$ and $R_5$ are the same or different and each is independently a hydrogen atom, a lower alkyl group, a lower alkoxyl group or a phenyl group.

(30) The method of (28), comprising deprotecting the compound represented by the formula (I) to form a compound represented by the formula (II):

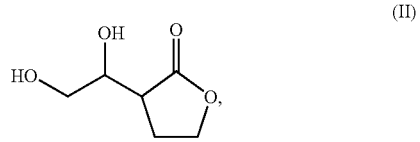

(II)

and converting the compound represented by the formula (II) to the compound represented by the formula (III).

(31) A method for producing a compound represented by the formula (V):

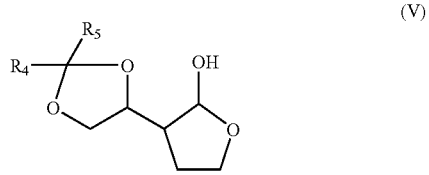

(V)

wherein $R_4$ and $R_5$ are the same or different and each is independently a hydrogen atom, a lower alkyl group, a lower alkoxyl group or a phenyl group, or $R_4$ and $R_5$ are optionally taken together to form an α,ω-alkylene group having 2 to 5 carbon atoms, wherein one of the carbon atoms at positions other than α-position and ω-position is optionally substituted by an oxygen atom or a sulfur atom, which comprises reducing a compound represented by the formula (III).

(32) The method of (31), wherein $R_4$ and $R_5$ are the same or different and each is independently a hydrogen atom, a lower alkyl group, a lower alkoxyl group or a phenyl group.

(33) A method of producing a compound represented by the formula (XIV), which comprises deprotecting and cyclizing a compound represented by the formula (V).

(34) The method of (33), wherein $R_4$ and $R_5$ are the same or different and each is independently a hydrogen atom, a lower alkyl group, a lower alkoxyl group or a phenyl group.

(35) A method for producing a compound represented by the formula (IV):

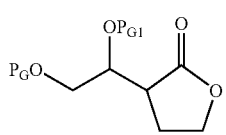

(IV)

wherein $P_G$ and $P_{G1}$ are the same or different and each is independently a hydroxy-protecting group, which comprises protecting a hydroxyl group of a compound represented by the formula (I).

(36) A method for producing a compound represented by the formula (VI):

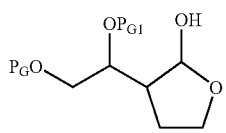

(VI)

wherein $P_G$ and $P_{G1}$ are the same or different and each is independently a hydroxy-protecting group, which comprises reducing a compound represented by the formula (IV).

(37) A method for producing a compound represented by the formula (XIV), which comprises deprotecting and cyclizing a compound represented by the formula (VI).

(38) A method for producing a compound represented by the formula (XIV), which comprises either the following step (1A) or (1B);

(1A) a step comprising obtaining a compound represented by the formula (III) from a compound represented by the formula (I), reducing the compound represented by the formula (III) to form a compound represented by the formula (V), and deprotecting and cyclizing the obtained compound represented by the formula (V) to form the compound represented by the formula (XIV), (1B) a step comprising protecting a hydroxyl group of the compound represented by the formula (I) to form a compound represented by the formula (IV), reducing the compound represented by the formula (IV) to form a compound represented by the formula (VI), and deprotecting and cyclizing the compound represented by the formula (VI) to form the compound represented by the formula (XIV).

(39) The method of (38), wherein $R_4$ and $R_5$ are the same or different and each is independently a hydrogen atom, a lower alkyl group, a lower alkoxyl group or a phenyl group.

(40) The method of (38), wherein, in step (1A), the compound represented by the formula (I) is deprotected to form a compound represented by the formula (II) and the compound represented by the formula (II) is converted to the compound represented by the formula (III).

(41) The method of (38) or (40), wherein the compound represented by the formula (I) is a compound having a relative configuration represented by the formula (VII), and the compound represented by the formula (XIV) is a compound having a relative configuration represented by the formula (XV).

(42) The method of (38) or (40), wherein the compound represented by the formula (I) is a compound having an absolute configuration represented by the formula (VII), and the compound represented by the formula (XIV) is a compound having an absolute configuration represented by the formula (XV), or the compound represented by the formula (I) is an enantiomer of the compound having an absolute configuration represented by the formula (VII), and the compound represented by the formula (XIV) is an enantiomer of the compound having an absolute configuration represented by the formula (XV).

(43) A method for producing a compound represented by the formula (XIX), which comprises the use of a compound represented by the formula (XIII).

(44) A method for producing a compound represented by the formula (XX), which comprises hydrolysis of a compound represented by the formula (XIX).

(45) The method of (44), which comprises addition of an organic amine after hydrolysis.

(46) The method of (44), wherein the compound represented by the formula (XIX) is produced using a compound represented by the formula (XIII).

(47) A method for producing a compound represented by the formula (III), which comprises acetalization or ketalization and lactonization after deprotection of $P_G$ and $R_3$ of a compound represented by the formula (XX).

(48) The method of (47), wherein $R_4$ and $R_5$ are the same or different and each is independently a hydrogen atom, a lower alkyl group, a lower alkoxyl group or a phenyl group.

(49) The method of (47), wherein the compound represented by the formula (XX) is obtained using a compound represented by the formula (XIII) as a starting material.

(50) A method for producing a compound represented by the formula (XIV), which comprises obtaining a compound represented by the formula (XIX) using a compound represented by the formula (XIII), hydrolyzing the obtained compound represented by the formula (XIX) to form a compound represented by the formula (XX), deprotecting $P_G$ and $R_3$ of the compound represented by the formula (XX), thereafter acetalizing or ketalizing and lactonizing the compound to form a compound represented by the formula (III), reducing the compound represented by the formula (III) to form a compound represented by the formula (V) and deprotecting and cyclizing the compound represented by the formula (V).

(51) The method of (50), wherein $R_4$ and $R_5$ are the same or different and each is independently a hydrogen atom, a lower alkyl group, a lower alkoxyl group or a phenyl group.

(52) The method of (50), wherein the compound represented by the formula (XIII) is a compound represented by the formula (XVI), the compound represented by the formula (XIX) is a compound having an absolute configuration represented by the formula (XVII), the compound represented by the formula (XX) is a compound having an absolute configuration represented by the formula (XVIII), the compound represented by the formula (III) is a compound having an absolute configuration represented by the formula (IX):

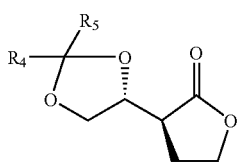

(IX)

wherein $R_4$ and $R_5$ are as defined in (50), the compound represented by the formula (V) is a compound having an absolute configuration represented by the formula (XI):

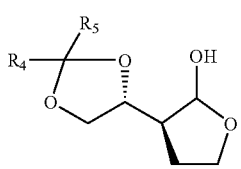

(XI)

wherein $R_4$ and $R_5$ are as defined in (50), and the compound represented by the formula (XIV) is a compound having an absolute configuration represented by the formula (XV), or the compound represented by the formula (XIII) is an enantiomer of the compound represented by the formula (XVI), the compound represented by the formula (XIX) is an enantiomer of the compound having an absolute configuration represented by the formula (XVII), the compound represented by the formula (XX) is an enantiomer of the compound having an absolute configuration represented by the formula (XVIII), the compound represented by the formula (III) is an enantiomer of the compound having an absolute configuration represented by the formula (IX), the compound represented by the formula (V) is an enantiomer of the compound having an absolute configuration represented by the formula (XI), and the compound represented by the formula (XIV) is an enantiomer of the compound having an absolute configuration represented by the formula (XV).

(53) A method for producing a compound having a relative configuration represented by the formula (XXII), which comprises stereoselective reduction of a compound represented by the formula (XXI).

(54) The method of (53), wherein the compound having a relative configuration represented by the formula (XXII) is a compound having an absolute configuration represented by the formula (XXII) or an enantiomer thereof.

(55) A production method of a compound having a relative configuration represented by the formula (XXIV):

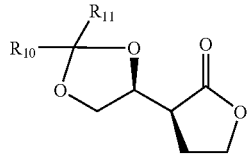

(XXIV)

wherein $R_{10}$ and $R_{11}$ are the same or different and each is independently a hydrogen atom, a lower alkyl group, a lower alkoxyl group or a phenyl group, or $R_{10}$ and $R_{11}$, are optionally taken together to form an α,ω-alkylene group having 2 to 5 carbon atoms, wherein one of the carbon atoms at positions other than α-position and ω-position is optionally substituted by an oxygen atom or a sulfur atom, which comprises the following step (2A) or (2B):

(2A) simultaneously deprotecting a compound having a relative configuration represented by the formula (XXII) and introducing a diol protecting group into the compound having a relative configuration represented by the formula (XXII) to produce the compound having a relative configuration represented by the formula (XXIV)

(2B) deprotecting the compound having a relative configuration represented by the formula (XXII) to form a compound having a relative configuration represented by the formula (XXIII):

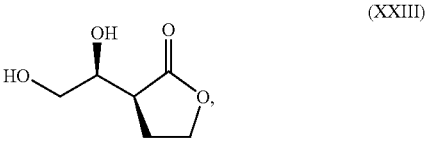

(XXIII)

introducing a diol protecting group into the compound having a relative configuration represented by the formula (XXIII), to produce the compound having a relative configuration represented by the formula (XXIV).

(56) The method of (55), wherein $R_{10}$ and $R_{11}$ are the same or different and each is independently a hydrogen atom, a lower alkyl group, a lower alkoxyl group or a phenyl group.

(57) A method for producing a compound having a relative configuration represented by the formula (XXV):

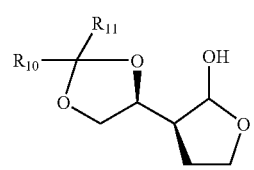

(XXV)

wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an α,ω-alkylene group having 2 to 5 carbon atoms, wherein one of the carbon atoms at positions other than α-position and ω-position is optionally substituted by an oxygen atom or a sulfur atom, which comprises reducing a compound having a relative configuration represented by the formula (XXIV).

(58) The method of (57), wherein $R_{10}$ and $R_{11}$ are the same or different and each is independently a hydrogen atom, a lower alkyl group, a lower alkoxyl group or a phenyl group.

(59) A method for producing a compound having a relative configuration represented by the formula (XXVI), which comprises deprotecting and cyclizing a compound having a relative configuration represented by the formula (XXV).

(60) The method of (59), wherein $R_{10}$ and $R_{11}$, are the same or different and each is independently a hydrogen atom, a lower alkyl group, a lower alkoxyl group or a phenyl group.

(61) A method for producing a compound having a relative configuration represented by the formula (XXVI), which comprises stereoselectively reducing a compound represented by the formula (XXI) to form a compound having a relative configuration represented by the formula (XXII), obtaining a compound having a relative configuration represented by the formula (XXIV) using the compound having a relative configuration represented by the formula (XXII), reducing the obtained compound having a relative configuration represented by the formula (XXIV) to form a compound having a relative configuration represented by the formula (XXV), and deprotecting and cyclizing the compound having a relative configuration represented by the formula (XXV).

(62) The method of (61), wherein $R_{10}$ and $R_{11}$ are the same or different and each is independently a hydrogen atom, a lower alkyl group, a lower alkoxyl group or a phenyl group.

(63) The method of (61), wherein the compound of formula (XXII) is a compound having an absolute configuration represented by the formula (XXII), the compound of formula (XXIV) is a compound having an absolute configuration represented by the formula (XXIV), the compound of formula (XXV) is a compound having an absolute configuration represented by the formula (XXV), and the compound of formula (XXVI) is a compound having an absolute configuration represented by the formula (XXVI), or the compound of formula (XXII) is an enantiomer of the compound having an absolute configuration represented by the formula (XXII), the compound of formula (XXIV) is an enantiomer of the compound having an absolute configuration represented by the formula (XXIV), the compound of formula (XXV) is an enantiomer of the compound having an absolute configuration represented by the formula (XXV), and the compound of formula (XXVI) is an enantiomer of the compound having an absolute configuration represented by the formula (XXVI).

(64) The method of (53), (54), (61) or (63), wherein the stereoselective reduction is an asymmetric hydrogenation reaction using a transition metal catalyst having an asymmetric ligand.

(65) The method of (64), wherein the transition metal catalyst has an asymmetric ligand which is an optically active phosphine derivative selected from the group consisting of the compounds represented by the following formulas:

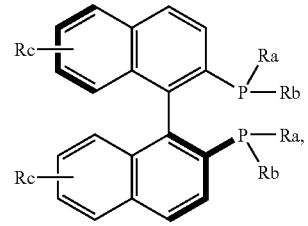

(L1)

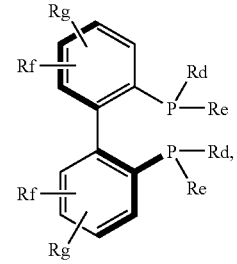

(L2)

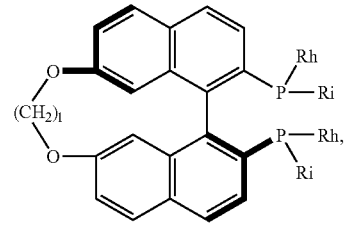

(L3)

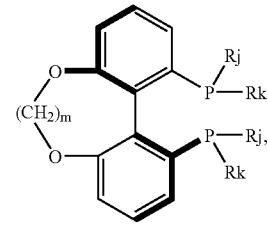

(L4)

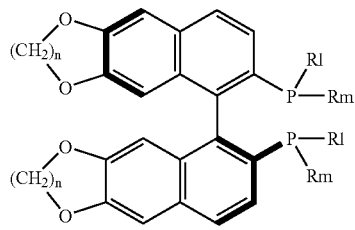

(L5) and

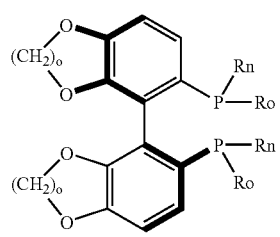

(L6)

wherein Ra, Rb, Rd, Re, Rh, Ri, Rj, Rk, Rl, Rm, Rn and Ro are the same or different and each is independently an optionally substituted phenyl or an optionally substituted cyclohexyl, Rc, Rf and Rg are the same or different and each is independently a hydrogen atom, a halogen atom, alkyl, alkoxy or an optionally substituted phenyl and l, m, n and o are each independently an integer of 1-6, (hereinafter to be also respectively referred to as compounds (L1)-(L6)) and enantiomers thereof, and a transition metal, which is ruthenium.

(66) The method of (65), wherein the asymmetric ligand is an optically active phosphine derivative selected from the group consisting of the compounds of the formulas (L1), (L2), (L3), (L4), (L5) and (L6), and the compound of formula (XXII) is a compound having an absolute configuration represented by the formula (XXII), or an asymmetric ligand is an optically active phosphine derivative selected from the group consisting of enantiomers of the compounds of the formulas (L1), (L2), (L3), (L4), (L5) and (L6), and the compound of formula (XXII) is an enantiomer of the compound having an absolute configuration represented by the formula (XXII).

(67) A method for producing a compound having a relative configuration represented by the formula (XV), which comprises deprotecting and cyclizing a compound having a relative configuration represented by the formula (XXV) to form a compound having a relative configuration represented by the formula (XXVI):

and inverting a hydroxyl group of a compound having a relative configuration represented by the formula (XXVI).

(68) The method of (67), wherein inverting the hydroxyl group of the compound having a relative configuration represented by the formula (XXVI) comprises the following step (2C) or (2D):

(2C) oxidizing the compound having a relative configuration represented by the formula (XXVI) to give a compound having a relative configuration represented by the formula (XXVII):

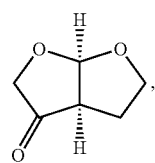

(XXVII)

reducing the compound having a relative configuration represented by the formula (XXVII) to form the compound having a relative configuration represented by the formula (XV), (2D) inversion esterification of the compound having a relative configuration represented by the formula (XXVI) to form a compound having a relative configuration represented by the formula (XXVIII):

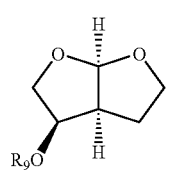

(XXVIII)

wherein $R_9$ is alkanoyl group wherein hydrogen atom is optionally substituted by fluorine atom or chlorine atom, or a benzoyl group wherein hydrogen atom of phenyl group is optionally substituted by nitro group, halogen, alkyl group, alkoxyl group or phenyl group, and hydrolyzing the obtained compound having a relative configuration represented by the formula (XXVIII) to form the compound having a relative configuration represented by the formula (XV).

(69) The method of (68), wherein the inversion esterification in step (2D) is carried out in the presence of triphenylphosphine or trialkylphosphine and azodicarboxylic acid ester or azodicarboxylic amide.

(70) The method of (67)-(69), wherein the compound of formula (XXVI) is a compound having an absolute configuration represented by the formula (XXVI), and the compound of formula (XV) is a compound having an absolute configuration represented by the formula (XV), or the compound of formula (XXVI) is an enantiomer of the compound having an absolute configuration represented by the formula (XXVI), and the compound of formula (XV) is an enantiomer of the compound having an absolute configuration represented by the formula (XV).

(71) The method of (67), wherein $R_{10}$ and $R_{11}$ are the same or different and each is independently a hydrogen atom, a lower alkyl group, a lower alkoxyl group or a phenyl group.

(72) The method of (67)-(71), wherein the compound having a relative configuration represented by the formula (XXV) is obtained by stereoselectively reducing a compound represented by the formula (XXI) to form a compound having a relative configuration represented by the formula (XXII), obtaining a compound having a relative configuration represented by the formula (XXIV) using the compound having a relative configuration represented by the formula (XXII), and reducing the compound having a relative configuration represented by the formula (XXIV).

(73) The method of (72), wherein the compound of formula (XXII) is a compound having an absolute configuration represented by the formula (XXII), the compound of formula (XXIV) is a compound having an absolute configuration represented by the formula (XXIV), the compound of formula (XXV) is a compound having an absolute configuration represented by the formula (XXV), and the compound of formula (XXVI) is a compound having an absolute configuration represented by the formula (XXVI), or the compound of formula (XXII) is an enantiomer of the compound having an absolute configuration represented by the formula (XXII), the compound of formula (XXIV) is an enantiomer of the compound having an absolute configuration represented by the formula (XXIV), the compound of formula (XXV) is an enantiomer of the compound having an absolute configuration represented by the formula (XXV), and the compound of formula (XXVI) is an enantiomer of the compound having an absolute configuration represented by the formula (XXVI).

(74) The method of (73), wherein the stereoselective reduction is an asymmetric hydrogenation reaction using a transition metal catalyst having an asymmetric ligand.

(75) The method of (74), wherein the transition metal catalyst has an asymmetric ligand which is an optically active phosphine derivative selected from the group consisting of the compounds represented by the following formulas:

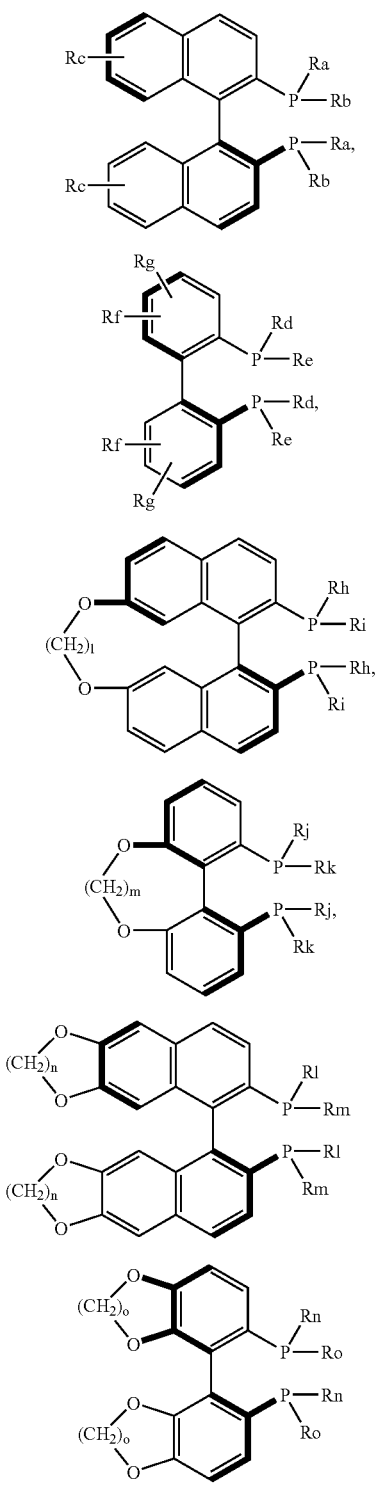

wherein Ra, Rb, Rd, Re, Rh, Ri, Rj, Rk, Rl, Rm, Rn and Ro are the same or different and each is independently an optionally substituted phenyl or an optionally substituted cyclohexyl, Rc, Rf and Rg are the same or different and each is independently a hydrogen atom, a halogen atom, alkyl, alkoxy or an optionally substituted phenyl and l, m, n and o are each independently an integer of 1-6, and enantiomers thereof, and a transition metal, which is ruthenium.

(76) The method of (75), wherein the asymmetric ligand is an optically active phosphine derivative selected from the group consisting of the compounds of the formulas (L1), (L2), (L3), (L4), (L5) and (L6), and the compound of formula (XXII) is a compound having an absolute configuration represented by the formula (XXII), or an asymmetric ligand is an optically active phosphine derivative selected from the group consisting of enantiomers of the compounds of the formulas (L1), (L2), (L3), (L4), (L5) and (L6), and the compound of formula (XXII) is an enantiomer of the compound having an absolute configuration represented by the formula (XXII).

(77) A method for producing a compound having a relative configuration represented by the formula (XV), which comprises inverting a hydroxyl group of a compound having a relative configuration represented by the formula (XXVI).

(78) The method of (77), which comprises the following step (2C) or (2D):

(2C) oxidizing the compound having a relative configuration represented by the formula (XXVI) to form a compound having a relative configuration represented by the formula (XXVII):

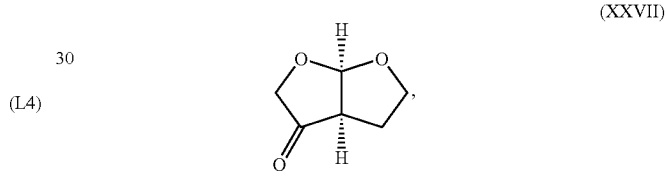

reducing the compound having a relative configuration represented by the formula (XXVII) to form the compound having a relative configuration represented by the formula (XV), (2D) inversion esterification of the compound having a relative configuration represented by the formula (XXVI) to form a compound having a relative configuration represented by the formula (XXVIII):

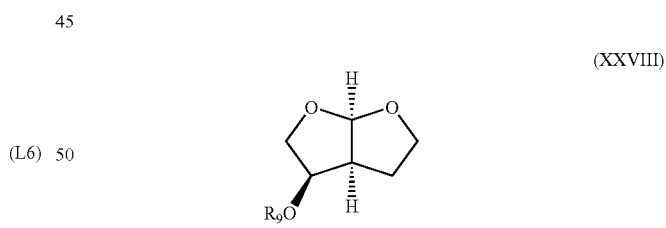

wherein $R_9$ is alkanoyl group wherein hydrogen atom is optionally substituted by fluorine atom or chlorine atom, or a benzoyl group wherein hydrogen atom of phenyl group is optionally substituted by nitro group, halogen, alkyl group, alkoxyl group or phenyl group, and hydrolyzing the compound having a relative configuration represented by the formula (XXVIII) to form the compound having a relative configuration represented by the formula (XV).

(79) The method of (78), wherein the inversion esterification in step (2D) is carried out in the presence of triphenylphosphine or trialkylphosphine and azodicarboxylic acid ester or azodicarboxylic amide.

(80) The method of (77)-(79), wherein the compound of formula (XXVI) is a compound having an absolute configuration represented by the formula (XXVI), and the compound of formula (XV) is a compound having an absolute configuration represented by the formula (XV), or the compound of formula (XXVI) is an enantiomer of the compound having an absolute configuration represented by the formula (XXVI), and the compound of formula (XV) is an enantiomer of the compound having an absolute configuration represented by the formula (XV).

DETAILED DESCRIPTION OF THE INVENTION

In the following, the compounds represented by the formulas (A), (B), (C), (I)-(VI), (XIII), (XIX) and (XX) are sometimes to be referred to as compounds (A), (B), (C), (I)-(VI), (XIII), (XIX) and (XX), respectively.

The configuration of compounds (A), (B), (C), (I)-(VI), (XIX) and (XX) of the present invention is not particularly limited and can encompass individual isomers or a mixture thereof at an optional proportion.

The configuration of compounds (XIII) and (XIV) is not particularly limited unless particularly indicated, and can encompass individual isomers or mixtures thereof at an optional proportion.

The optically active form in the context of the present specification is used to mean non-racemic. For example, the optically active form includes a mixture of 70% S-form and 30% R-form and a mixture of 70% (S,S)-form and 30% (R,R)-form.

As compound (A), for example, compounds (I), (II), (III), (IV) and the like can be mentioned. As compound (B), for example, compounds (V), (VI) and the like can be mentioned. As compound (C), for example, compounds (XIX), (XX) and the like can be mentioned.

As a compound whose relative configuration is represented by the formula (D), for example, compounds whose relative configurations are represented by the formulas:

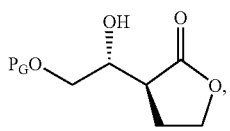
(VII)

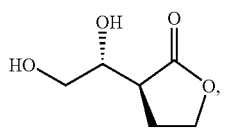
(VIII)

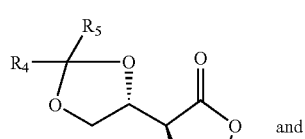
(IX)

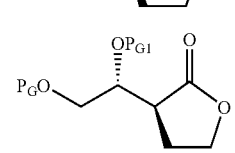
(X)

wherein each symbol is as defined above, and the like can be mentioned.

As a compound whose relative configuration is represented by the formula (E), for example, compounds whose relative configurations are represented by the formulas:

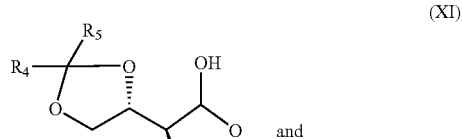
(XI)

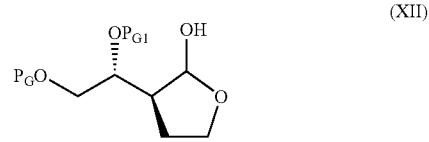
(XII)

wherein each symbol is as defined above, and the like can be mentioned.

As a preferable compound whose absolute configuration is represented by the formula (D), for example, a compound whose absolute configuration is represented by the formula:

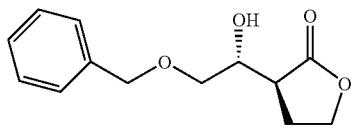

and the like can be mentioned.

As a compound whose absolute configuration is represented by the formula (F), for example, compounds whose absolute configurations are represented by the formulas (XVII) and (XVIII) and the like can be mentioned, and as a preferable compound whose absolute configuration is represented by the formula (F), compounds whose absolute configurations are represented by the formulas:

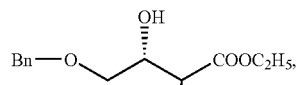

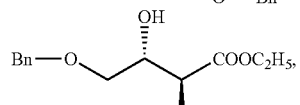

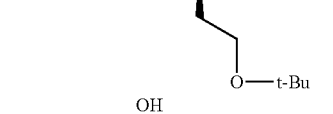

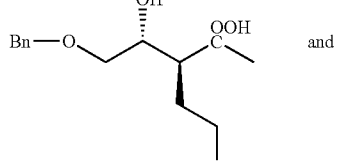

-continued

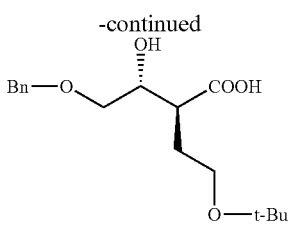

wherein —Bn is a benzyl group and -t-Bu is a t-butyl group, and the like can be mentioned.

As the salts of the compounds represented by the formulas (C) and (F), for example, salts with a base such as organic amine (e.g., dibenzylamine, benzylamine, dicyclohexylamine, cyclohexylamine, (S)-phenethylamine etc.), an alkali metal (e.g., potassium, sodium, lithium etc.), an alkaline earth metal (e.g., magnesium, calcium, barium etc.) and a basic amino acid (e.g., L-phenylalanine methyl ester, glycine methyl ester etc.) can be mentioned. Preferred are a salt with organic amine and a salt with an alkali metal, and particularly preferred are dibenzylamine salt and potassium salt. The organic amine and basic amino acid may be racemates or optical isomers.

The compound whose relative configuration is represented by the formula (D) refers to a compound whose absolute configuration is represented by the formula (D) or an enantiomer thereof, or a mixture of a compound whose absolute configuration is represented by the formula (D) and an enantiomer thereof at an optional proportion (including racemates).

The relative configuration of the compound whose relative configuration is represented by the formula (E), the compound having a relative configuration represented by the formula (VII), the compound having a relative configuration represented by the formula (XV) and the like means the same as in the compound whose relative configuration is represented by the formula (D).

In the formulas (A), (B), (C), (D), (E), (F), (I), (IV), (VI), (VII), (X), (XII), (XIII) and (XVI)-(XX), the hydroxy-protecting group for R, $R_1$, $R_3$, $P_G$ and $P_{G1}$ is exemplified by benzyl group, t-butyl group, 1-ethoxyethyl group, 3,4,5,6-tetrahydro-2H-pyran-2-yl group, triphenylmethyl group, 1-methoxy-1-methylethyl group, methoxymethyl group, ethoxymethyl group, triethylsilyl group, tri-n-butylsilyl group, t-butyldimethylsilyl group and the like, wherein R and $P_G$ are preferably benzyl group, t-butyl group and triphenylmethyl group, and $R_1$ and $P_{G1}$ are preferably 1-ethoxyethyl group and 3,4,5,6-tetrahydro-2H-pyran-2-yl group. $R_3$ is preferably benzyl group or t-butyl group.

However, when, in the formula (A), $R_1$ is a hydrogen atom, R is a hydroxy-protecting group, and the relative configuration of compound (A) is syn, i.e., the relative configuration of compound (A) is represented by

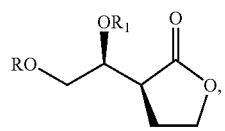

R is a hydroxy-protecting group other than benzyl group.

In the formulas (A), (B), (D), (E), (III), (V), (IX) and (XI), the lower alkyl group for $R_4$ and $R_5$ is, for example, a straight chain or branched chain alkyl group having 1 to 6, preferably 1 to 3, carbon atoms, which is specifically, for example, methyl group, ethyl group, n-propyl group, isopropyl group and the like, wherein $R_4$ and $R_5$ are each preferably a methyl group.

In the formulas (A), (B), (D), (E), (III), (V), (IX) and (XI), the lower alkoxyl group for $R_4$ and $R_5$ is, for example, a straight chain or branched chain alkoxyl group having 1 to 6, preferably 1 to 3, carbon atoms, which is specifically, for example, methoxy group, ethoxy group, n-propoxy group, isopropoxy group and the like.

In the formulas (A), (B), (D), (E), (III), (V), (IX) and (XI), as the α,ω-alkylene group having 2 to 5 carbon atoms, wherein one of the carbon atoms at positions other than α-position and ω-position is optionally substituted by an oxygen atom or a sulfur atom, which is formed by $R_4$ and $R_5$ in combination, for example, ethylene group, 1,3-propylene group, 1,4-butylene group, 1,5-pentylene group, 2-oxa-1,4-butylene group, 3-oxa-1,5-pentylene group, 2-thia-1,4-butylene group, 3-thia-1,5-pentylene group and the like can be mentioned.

In the formulas (C), (F), (XIII), (XVI), (XVII) and (XIX), the lower alkoxyl group for $R_6$ and $R_2$ is, for example, a straight chain or branched chain alkoxy group having 1 to 6, preferably 1 to 4, carbon atoms, which is specifically, for example, methoxy group, ethoxy group, n-propoxy group, isopropoxy group, n-butoxy group, t-butoxy group and the like, with preference given to methoxy group.

In the formulas (C), (F), (XIII), (XVI), (XVII) and (XIX), the lower alkylthio group for $R_6$ and $R_2$ is, for example, a straight chain or branched chain alkylthio group having 1 to 6, preferably 1 to 4, carbon atoms, which is specifically, for example, methylthio group, ethylthio group, n-propylthio group, isopropylthio group, n-butylthio group, t-butylthio group and the like.

The compound having a relative configuration represented by the formula (XXII) refers to a compound whose absolute configuration is represented by the formula (XXII) or an enantiomer thereof, or a mixture of a compound whose absolute configuration is represented by the formula (XXII) and an enantiomer thereof at an optional proportion (including racemates). The compounds having relative configurations represented by the formulas (G), (H), (XXIII)-(XXVIII) and (XV) mean the same as in the compound having relative configuration represented by the aforementioned formula (XXII). The compounds having relative configurations represented by the formulas (G), (H) and (XXII)-(XXVIII) are referred to as compounds (G), (H) and (XXII)-(XXVIII), respectively. The compound having a relative configuration represented by the formula (XV) is also referred to as compound (XV).

As the compound (G), for example, compounds (XXII)-(XXIV) and the like can be mentioned. As the compound (H), for example, compound (XXV) and the like can be mentioned.

In the formulas (G) and (H), the hydroxy-protecting group for $R_7$ and $R_8$ is, for example, benzyl group, tert-butyl group, 1-ethoxyethyl group, 3,4,5,6-tetrahydro-2H-pyran-2-yl group, triphenylmethyl group, 1-methoxy-1-methylethyl group, methoxymethyl group, ethoxymethyl group, triethylsilyl group, tri-n-butylsilyl group, tert-butyldimethylsilyl group and the like. As $R_7$, benzyl group, tert-butyl group and triphenylmethyl group are preferable. As $R_8$, 1-ethoxyethyl group and 3,4,5,6-tetrahydro-2H-pyran-2-yl group are preferable. As the hydroxy-protecting group for $P_{G2}$ in the formulas (XXI) and (XXII), the protecting groups mentioned for $R_7$ of formulas (G) and (H) can be used.

However, for the compound (G) of the present invention, when, in the formula (G), $R_8$ is a hydrogen atom and $R_7$ is a hydroxy-protecting group, $R_7$ is a hydroxy-protecting group other than benzyl group.

In the formulas (G), (H), (XXIV) and (XXV), the lower alkyl group for $R_{10}$ and $R_{11}$ is, for example, a straight chain or branched chain alkyl group having 1 to 6, preferably 1 to 3, carbon atoms, which is specifically, for example, methyl group, ethyl group, n-propyl group, isopropyl group and the like, wherein $R_{10}$ and $R_{11}$ are each preferably a methyl group.

In the formulas (G), (H), (XXIV) and (XXV), the lower alkoxyl group for $R_{10}$ and $R_{11}$ is, for example, a straight chain or branched chain alkoxyl group having 1 to 6, preferably 1 to 3, carbon atoms, which is specifically, for example, a methoxy group, an ethoxy group, an n-propoxy group, an isopropoxy group and the like.

In the formulas (G), (H), (XXIV) and (XXV), as the α,ω-alkylene group having 2 to 5 carbon atoms, wherein one of the carbon atoms at positions other than α-position and ω-position is optionally substituted by an oxygen atom or a sulfur atom, which is formed by $R_{10}$ and $R_{11}$ in combination, for example, ethylene group, 1,3-propylene group, 1,4-butylene group, 1,5-pentylene group, 2-oxa-1,4-butylene group, 3-oxa-1,5-pentylene group, 2-thia-1,4-butylene group, 3-thia-1,5-pentylene group and the like can be mentioned.

In the formula (XXVIII), the alkanoyl group of alkanoyl group for $R_9$ wherein hydrogen atom is optionally substituted by fluorine atom or chlorine atom is, for example, a straight chain or branched chain alkanoyl group having 1 to 7, preferably 1 to 5, carbon atoms. As the alkanoyl group wherein hydrogen atom is optionally substituted by fluorine atom or chlorine atom, for example, formyl, acetyl, chloroacetyl, trifluoroacetyl, propanoyl, butanoyl, isobutanoyl, pivaloyl and the like, preferably, acetyl, trifluoroacetyl, pivaloyl and the like, can be mentioned. The number of the substituents is not particularly limited, but 1-3 is preferable, which substituents may be the same or different.

In the formula (XXVIII), the number of the substituents of the benzoyl group for $R_9$ wherein hydrogen atom of phenyl group is optionally substituted by nitro group, halogen, alkyl group, alkoxyl group or phenyl group is not particularly limited, but 1-3 is preferable, which substituents may be the same or different. As the halogen for the substituent, fluorine atom, chlorine atom, bromine atom and iodine atom can be mentioned, with preference given to fluorine atom, chlorine atom and the like. As the alkyl group for the substituent, for example, a straight chain or branched chain alkyl group having 1 to 6, preferably 1 to 4, carbon atoms can be mentioned, such as methyl, ethyl, propyl, isopropyl, butyl, isobutyl, sec-butyl, tert-butyl, pentyl, isopentyl, neopentyl, hexyl, isohexyl and the like, with preference given to methyl, ethyl, tert-butyl and the like. As the alkoxyl group for the substituent, for example, a straight chain or branched chain alkoxyl group having 1 to 8, preferably 1 to 4, carbon atoms can be mentioned, such as methoxy, ethoxy, propoxy, isopropoxy, butoxy, isobutoxy, sec-butoxy, tert-butoxy and the like, with preference given to methoxy, ethoxy, tert-butoxy and the like.

The methods for producing a compound (XIV) of the present invention, particularly a compound represented by the formula (XV), are explained in detail in the following. The methods are shown in the following Scheme 1. Particularly, the methods for producing a compound, whose relative configuration or absolute configuration is represented by the formula (XV), are shown in Scheme 2.

The present invention is characterized by a method comprising hydroxyethylation of compound (XIII), followed by cyclization to form compound (I); a method for producing compound (III) using compound (I) as a material; a method for producing compound (V) by reducing compound (III); and a method comprising deprotecting and cyclizing compound (V) to form compound (XIV). The present invention is also characterized by a method comprising protecting hydroxyl group of compound (I) to form compound (IV); a method comprising reducing compound (IV) to form compound (VI); and a method comprising deprotecting and cyclizing compound (VI) to form compound (XIV). The methods of the present invention can be each performed independently, but two or more of the methods are preferably performed in combination.

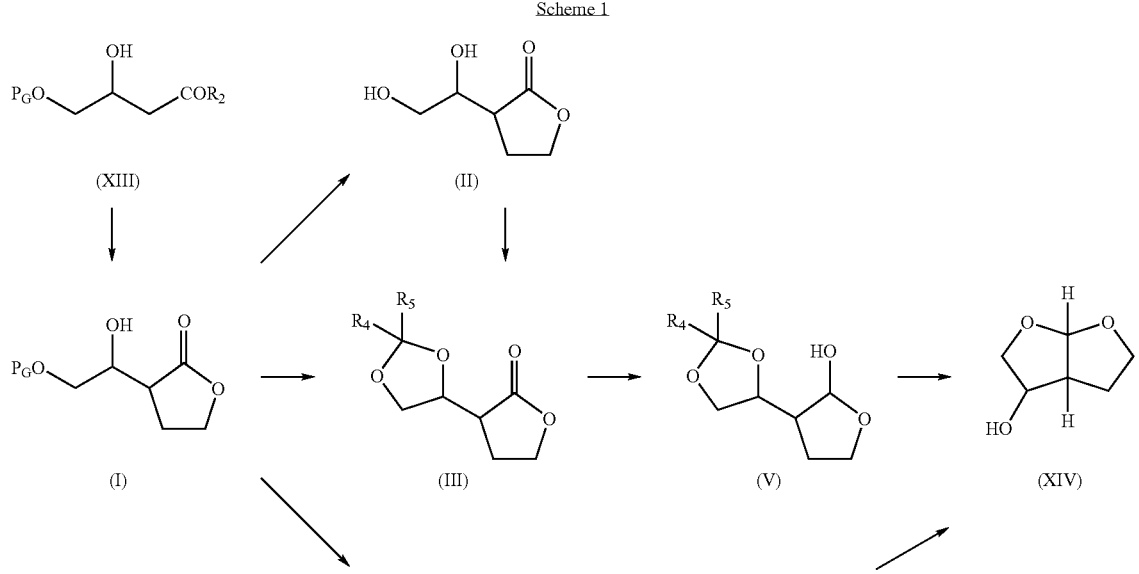

Scheme 1

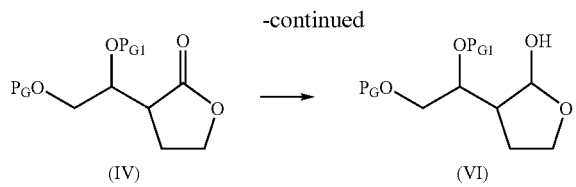

wherein each symbol is as defined above.

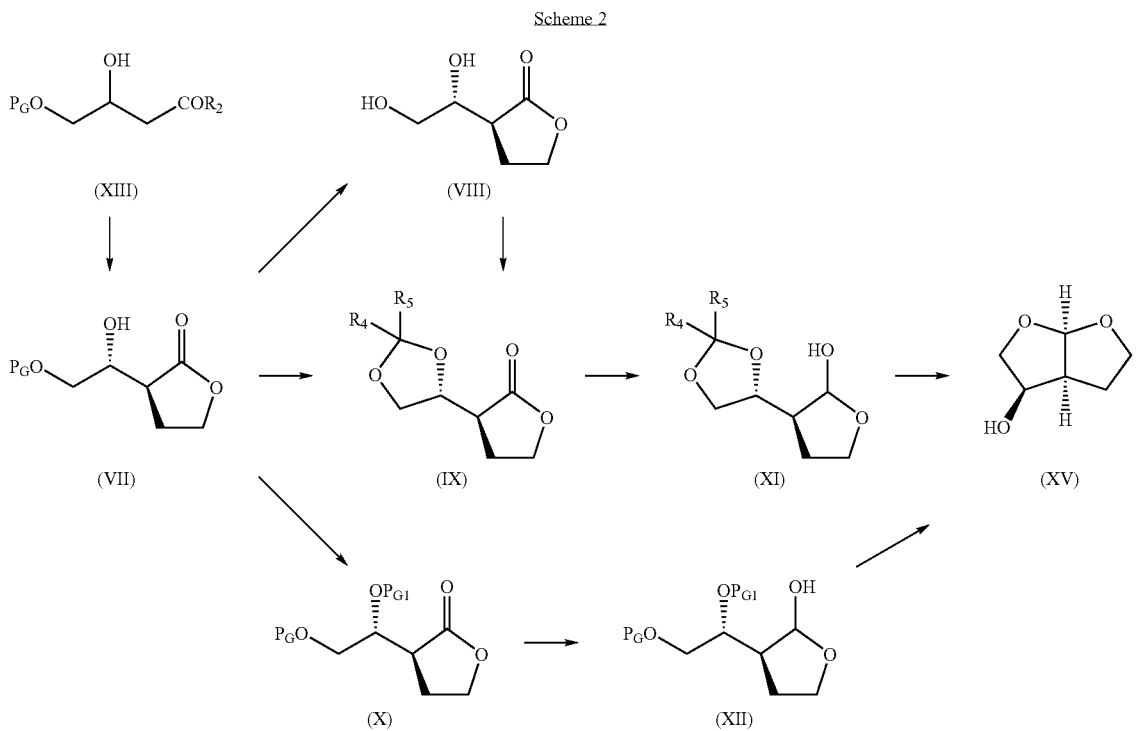

wherein each symbol is as defined above.

Production of Compound (I) from Compound (XIII)

The compound (XIII) can be obtained by a known method (e.g., method described in Heterocycles 26, 2841 (1987), U.S. Pat. No. 5,399,722 etc. and the like).

Regarding the optically active form of compound (XIII), the R-form of compound (XIII) (to be also referred to as a compound of the formula (XVI)) can be obtained according to a method described in, for example, Heterocycles 26, 2841 (1987) and the like, and the S-form (to be also referred to as an enantiomer of a compound of the formula (XVI)) can be obtained according to a method described in, for example, U.S. Pat. No. 5,399,722 and the like.

The compound (I) can be obtained by hydroxyethylation of compound (XIII), followed by cyclization. For example, compound (XIII) is reacted with 2-(1-ethoxyethoxy)ethyl halide, 2-(3,4,5,6-tetrahydro-2H-pyran-2-yloxy)ethyl halide, 2-vinyloxyethyl halide, 2-(t-butoxy)ethyl halide, 2-trimethylsilyloxyethyl halide, 2-triethylsilyloxyethyl halide, 2-t-butyldimethylsilyloxyethyl halide, ethylene oxide and the like, under addition of a base (e.g., lithium diisopropylamide, lithium hexamethyldisilazide, sodium hydride, potassium hydride and the like, preferably lithium diisopropylamide), and then cyclized.

The amount of the base to be used is generally 1.8-2.8 mol, preferably 2-2.4 mol, per 1 mol of compound (XIII).

As 2-(1-ethoxyethoxy)ethyl halide, for example, 2-(1-ethoxyethoxy)ethyl iodide, 2-(1-ethoxyethoxy)ethyl bromide and the like can be mentioned; as 2-(3,4,5,6-tetrahydro-2H-pyran-2-yloxy)ethyl halide, for example, 2-(3,4,5,6-tetrahydro-2H-pyran-2-yloxy)ethyl iodide, 2-(3,4,5,6-tetrahydro-2H-pyran-2-yloxy)ethyl bromide and the like can be mentioned; as 2-vinyloxyethyl halide, for example, 2-vinyloxyethyl iodide, 2-vinyloxyethyl bromide and the like can be mentioned; as 2-(t-butoxy)ethyl halide, for example, 2-(t-butoxy)ethyl iodide, 2-(t-butoxy)ethyl bromide and the like can be mentioned; as 2-trimethylsilyloxyethyl halide, for example, 2-trimethylsilyloxyethyl iodide, 2-trimethylsilyloxyethyl bromide and the like can be mentioned; as 2-triethylsilyloxyethyl halide, for example, 2-triethylsilyloxyethyl iodide, 2-triethylsilyloxyethyl bromide and the like can be mentioned; as 2-t-butyldimethylsilyloxyethyl halide, for example, 2-t-butyldimethylsilyloxyethyl iodide, 2-t-butyldimethylsilyloxyethyl bromide and the like can be mentioned. Of the reagents for the hydroxyethylation, 2-(1-ethoxyethoxy)ethyl iodide, 2-(3,4,5,6-tetrahydro-2H-pyran-2-yloxy)ethyl iodide, 2-vinyloxyethyl iodide, 2-(t-butoxy)ethyl iodide, 2-trimethylsilyloxyethyl iodide, 2-triethylsilyloxyethyl iodide, 2-t-butyldimethylsilyloxyethyl iodide and ethylene oxide are preferable.

The amount of the reagent to be used for hydroxyethylation, such as 2-(1-ethoxyethoxy)ethyl halide and the like, is generally 0.8-2 mol, preferably 1-1.5 mol, per 1 mol of compound (XIII).

The hydroxyethylation reaction is carried out in a reaction solvent such as tetrahydrofuran (THF), methyl t-butyl ether (MTBE), ethylene glycol dimethyl ether, diethylene glycol dimethyl ether, 1,3-dioxolane, 1,4-dioxane, methyl cyclopentyl ether and the like, preferably THF or MTBE. The amount of the reaction solvent to be used is 1-50 L, preferably 3-20 L, per 1 kg of compound (XIII).

The reaction temperature is generally −30° C. to 60° C., preferably 0 to 30° C., and the reaction time is generally 1 hr-48 hr, preferably 3 hr-24 hr.

The reagent for the hydroxyethylation can be produced by any suitable known method. For example, 2-(1-ethoxyethoxy)ethyl iodide can be produced by mixing 2-iodoethanol with ethyl vinyl ether in the presence of p-toluenesulfonic acid; 2-(3,4,5,6-tetrahydro-2H-pyran-2-yloxy)ethyl iodide can be produced by mixing 3,4-dihydro-2H-pyran with 2-iodoethanol in the presence of p-toluenesulfonic acid; 2-vinyloxyethyl iodide can be produced by reacting 2-vinyloxyethanol with p-toluenesulfonyl chloride in the presence of triethylamine, and then mixing with sodium iodide in the presence of sodium hydrogen carbonate; 2-(t-butoxy)ethyl iodide can be produced by mixing isobutylene with 2-iodoethanol in the presence of trifluoromethanesulfonic acid; 2-trimethylsilyloxyethyl iodide can be produced by mixing trimethylsilyl chloride with 2-iodoethanol in the presence of imidazole; 2-triethylsilyloxyethyl iodide can be produced by mixing triethylsilyl chloride with 2-iodoethanol in the presence of imidazole; and 2-t-butyl dimethylsilyloxyethyl iodide can be produced by mixing t-butyldimethylsilyl chloride with 2-iodoethanol in the presence of imidazole.

The compound (I) can be isolated by any suitable conventional method. For example, the compound can be isolated by pouring a reaction mixture into aqueous hydrochloric acid, partitioning the mixture, washing the obtained organic layer with aqueous alkali solution and evaporating the solvent. For complete cyclization, the isolation product may be reacted in a solvent in the presence of an acid catalyst such as p-toluenesulfonic acid and the like, and worked up by any suitable conventional method. The obtained isolate can be further purified by any suitable conventional method but may optionally be used in the next reaction without purification.

The compound (I) obtained by the above-mentioned method is mostly obtained as a compound having a relative configuration represented by the formula (VII). By recrystallization thereof from, for example, diisopropyl ether, a purer compound having a relative configuration represented by the formula (VII) can be obtained.

Using an optically active form of compound (XIII) for the above-mentioned method, a compound having an absolute configuration represented by the formula (VII) or an enantiomer thereof can be obtained, wherein the optically active form includes an S-form of compound (XIII), an R-form of compound (XIII), and a mixture of S-form and R-form except racemate. When an S-form of compound (XIII), i.e., a compound represented by the formula (XVI):

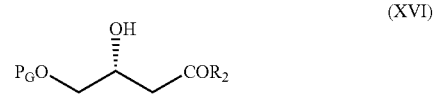

wherein each symbol is as defined above, is used, a compound having an absolute configuration represented by the formula (VII) can be obtained, and when an R-form of compound (XIII), i.e., a compound represented by the formula:

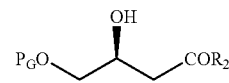

wherein each symbol is as defined above, is used, an enantiomer of a compound having an absolute configuration represented by the formula (VII) can be obtained. When a mixture of S-form and R-form at an optional proportion except racemate is used, a mixture of a compound having an absolute configuration represented by the formula (VII) and an enantiomer thereof can be obtained. By recrystallizing the reaction product using a suitable solvent such as diisopropyl ether, MTBE and the like, the proportion of either the compound having an absolute configuration represented by the formula (VII) or the enantiomer thereof can be increased.

Production of Compound (XIV) from Compound (I)

The compound (XIV) can be obtained by introducing a protecting group into compound (I), followed by reduction and cyclization. That is, the compound is obtained by a step of, for example, the following (1A) or (1B).

Step (1A) comprises obtaining compound (III) using compound (I), reducing the compound (III) to form compound (V), and deprotecting and cyclizing the compound (V) to form compound (XIV). In step (1B), the hydroxyl group of compound (I) is protected to form compound (IV), the compound (IV) is reduced to form compound (VI) and the compound (VI) is deprotected and cyclized to form compound (XIV).

Step (1A)

Production of Compound (III) from Compound (I)

The compound (III) can be produced by, for example, the following two methods using compound (I). The first method (hereinafter, Method (1)) comprises deprotecting compound (I) to form compound (II), introducing a diol-protecting group into the obtained compound (II) to form compound (III) and the second method (hereinafter, Method (2)) comprises directly protecting diol from compound (I) to form compound (III). Each method is explained in the following.

Method (1) (Method for Producing Compound (III) from Compound (I) Via Compound (II))

The compound (II) can be obtained by deprotection of compound (I). The deprotecting reagent can be appropriately selected depending on the kind of the protecting group of compound (I). When the protecting group is a t-butyl group, for example, compound (I) is reacted using an acid (e.g., trifluoroacetic acid, trifluoromethanesulfonic acid, methanesulfonic acid, strong acidic ion-exchange resin and the like, preferably trifluoroacetic acid) generally at −20° C. to 80° C., preferably 0° C. to 30° C., generally for 1 min-5 hr, preferably 15 min-3 hr, for deprotection. The acid is used in an amount of generally 0.01-10 L, preferably 0.1-5 L, per 1 kg of compound (I). After the completion of the reaction, compound (II) can be isolated by evaporating the acid or, after neutralization by a conventional method, by extracting with an organic solvent and evaporating the solvent.

When the protecting group is a benzyl group, for example, compound (I) is deprotected by a reaction in a solvent (e.g., ethyl acetate, ethanol, methanol, acetic acid, THF and the like, preferably ethyl acetate, acetic acid), using a catalyst (e.g., Pd/C, Pd(OH)$_2$ and the like, preferably Pd/C) generally at −20° C. to 100° C., preferably 0° C. to 50° C. under a hydrogen atmosphere generally for 0.5-12 hr, preferably 1-6 hr.

The amount of the solvent to be used is generally 1-50 L, preferably 3-25 L, per 1 kg of compound (I). The amount of the reduction catalyst to be used is generally 0.00001-0.5 kg, preferably 0.0001-0.2 kg, per 1 kg of compound (I).

The compound (II) can be isolated by evaporating the solvent after filtering off the catalyst.

The protecting reagent to be used for converting the compound (II) to compound (III) varies depending on the kind of $R_4$ and $R_5$, which are the constituent elements of the protecting group, and when, for example, both $R_4$ and $R_5$ are methyl groups, 2,2-dimethoxypropane or acetone can be used. In this case, the compound (II) can be protected by reacting the compound with 2,2-dimethoxypropane or acetone using an acid (e.g., p-toluenesulfonic acid, pyridinium p-toluenesulfonate, methanesulfonic acid, sulfuric acid, acidic ion-exchange resin, boron trifluoride and the like, preferably p-toluenesulfonic acid, pyridinium p-toluenesulfonate) generally at −20° C. to 100° C., preferably 0° C. to 50° C., for generally 0.5-12 hr, preferably 1-6 hr. When both $R_4$ and $R_5$ are lower alkyl groups, the reaction can be carried out according to the above-mentioned method.

The amount of the protecting reagent, such as 2,2-dimethoxypropane and the like, to be used is generally 0.5-50 L, preferably 3-20 L, per 1 kg of compound (II). The amount of the acid to be used is generally 0.0001-0.5 kg, preferably 0.0005-0.2 kg, per 1 kg of compound (II).

The compound (III) can be isolated by any suitable conventional method. For example, when an acid is used as mentioned above, the compound can be isolated by neutralizing the reaction mixture with an aqueous alkali solution, partitioning the mixture, washing the obtained organic layer with aqueous alkali solution and evaporating the solvent. The isolate can be purified by any suitable conventional method but may optionally be used in the next reaction without purification.

Method (2) (Method for Directly Producing Compound (III) from Compound (I))

The deprotection of compound (I) and protection of diol group are simultaneously conducted to directly obtain compound (III). While this method is performed by simultaneously adding a deprotecting reagent and a protecting reagent, which are used in the above-mentioned method (1), the reagents are appropriately determined according to the kinds of the group to be deprotected and the protecting group of diol.

As a non-limiting example, when the protecting group of compound (I) is a benzyl group and the diol-protecting group is a dimethylmethylene group, compound (I) and 2,2-dimethoxypropane and/or acetone, which is a protecting reagent, are reacted in a solvent (e.g., THF, ethyl acetate and the like, preferably THF) or without solvent, using a catalyst (e.g., Pd/C, Pd(OH)$_2$ and the like, preferably Pd/C) and an acidic ion-exchange resin (e.g., Amberlyst 15E (manufactured by Rohm & Haas), Nafion SAC13 (manufactured by Dupont) etc.) or an acid (e.g., phosphoric acid, hydrochloric acid, sulfuric acid, methanesulfonic acid, trifluoromethanesulfonic acid, p-toluenesulfonic acid, benzenesulfonic acid, boron trifluoride, phosphorus oxychloride etc.) generally at −20° C. to 100° C., preferably 0° C. to 50° C., under a hydrogen atmosphere generally for 0.5-12 hr, preferably 1-6 hr to form compound (III).

The amount of the protecting reagent, such as 2,2-dimethoxypropane and the like, to be used is generally 0.5-100 L, preferably 1-50 L, per 1 kg of compound (I). The amount of the reduction catalyst to be used is generally 0.0001-0.5 kg per 1 kg of compound (I). The amount of the acidic ion-exchange resin to be used is generally 0.001-0.5 kg, preferably 0.005-0.1 kg, per 1 kg of compound (I). When other acid is used, the amount of the acid to be used is generally 0.00001-0.1 kg, preferably 0.0001-0.01 kg, per 1 kg of compound (I). When a solvent is used, the amount of the solvent to be used is generally 0.5-50 L, preferably 1-25 L, per 1 kg of compound (I).

The compound (III) can be isolated by evaporating the solvent after filtering off the catalyst. The isolate can be purified by any suitable conventional method but optionally may be used in the next reaction without purification.

When $R_4$ is a hydrogen atom and $R_5$ is a lower alkyl group or a phenyl group, which are the constituent elements of the protecting group, the reaction can be carried out in the same manner as in the Methods (1) and (2), using alkanal or benzaldehyde, and/or acetal of alkanal or benzaldehyde (e.g., dimethyl acetal etc.) instead of 2,2-dimethoxypropane or acetone.

When $R_4$ is a lower alkyl group or a phenyl group and $R_5$ is a lower alkyl group or a phenyl group, the reaction can be generally carried out in the same manner as in Methods (1) and (2), using $R_4COR_5$ and/or acetal thereof (e.g., dimethyl acetal etc.) instead of 2,2-dimethoxypropane or acetone.

When $R_4$ is a lower alkyl group or a phenyl group and $R_5$ is a lower alkoxyl group, the reaction can be carried out in the same manner as in Methods (1) and (2), using trialkyl orthoalkanoate (e.g., MeC(OEt)$_3$ etc.) or trialkyl orthobenzoate instead of 2,2-dimethoxypropane or acetone.

When $R_4$ is a hydrogen atom and $R_5$ is a lower alkoxyl group, the reaction can be carried out in the same manner as in Methods (1) and (2), using trialkyl orthoformate instead of 2,2-dimethoxypropane or acetone.

When $R_4$ and $R_5$ are lower alkoxyl groups, the reaction can be carried out in the same manner as in Methods (1) and (2), using tetraalkyl orthocarbonate instead of 2,2-dimethoxypropane or acetone.

When $R_4$ and $R_5$ are taken together to form an α,ω-alkylene group having 2 to 5 carbon atoms, wherein one of the carbon atoms at positions other than α-position and ω-position is optionally substituted by an oxygen atom or a sulfur atom, the reaction can be carried out in the same manner as in methods (1), (2) using cyclopentanone, cyclohexanone, 1,1-dimethoxycyclohexane, 3-oxotetrahydrofuran, tetrahydro-4H-pyran-4-one, 3-oxotetrahydrothiophene, tetrahydrothiopyran-4-one and the like instead of 2,2-dimethoxypropane or acetone.

The compounds having relative configurations represented by the formulas (VIII) and (IX) can be produced according to the Methods (1) and (2), using a compound having a relative configuration represented by the formula (VII).

The compounds having absolute configurations represented by the formulas (VIII) and (IX) can be produced according to the Methods (1) and (2), using a compound having an absolute configuration represented by the formula (VII). The enantiomers of the compounds having absolute configurations represented by the formulas (VIII) and (IX) can be produced according to Methods (1) and (2), using an enantiomer of a compound having an absolute configuration represented by the formula (VII).

Production of Compound (V) from Compound (III)

The compound (V) can be obtained by reducing compound (III). The reduction reaction can be carried out according to a method generally used for reducing lactone to lactol. For example, the reaction is carried out using a reducing agent (e.g., diisobutylaluminum hydride (DIBAL-H), sodium bis-2-methoxyethoxyaluminum hydride, lithium aluminum tri-t-butoxyhydride and the like, preferably DIBAL-H, lithium aluminum tri-t-butoxyhydride) in a solvent (e.g., dichloromethane, toluene, THF, MTBE and the like, preferably dichloromethane, toluene, THF) at −100° C. to 50° C., preferably −80° C. to 0° C., for 10 min-6 hr, preferably 15 min-3 hr.

The amount of the reducing agent to be used is generally 0.8-1.5 mol, preferably 1-1.2 mol, per 1 mol of compound (III). The amount of the solvent to be used is generally 1-50 L, preferably 2-20 L, per 1 kg of compound (III).

The compound (V) can be isolated according to any suitable conventional method. For isolation, for example, a reaction mixture is poured into a saturated aqueous ammonium chloride solution, the mixture is partitioned, the obtained organic layer is dried over anhydrous magnesium sulfate and the like, and filtered, and the solvent is evaporated. The isolate can be purified by any suitable conventional method but may be used in the next reaction without purification.

The compound having a relative configuration represented by the formula (XI) can be produced according to the above-mentioned method using a compound having a relative configuration represented by the formula (IX).

The compound having an absolute configuration represented by the formula (XI) can be produced according to the above-mentioned method using a compound having an absolute configuration represented by the formula (IX) as a material. The enantiomer of a compound having an absolute configuration represented by the formula (XI) can be produced according to the above-mentioned method using an enantiomer of a compound having an absolute configuration represented by the formula (IX).

Production of Compound (XIV) from Compound (V)

The compound (XIV) can be obtained by deprotecting and cyclizing compound (V). For example, compound (V) can be deprotected and cyclized by reaction in a solvent (e.g., THF, 1,4-dioxane, MTBE, di-n-butyl ether, 1,2-dimethoxyethane, toluene and the like, preferably THF, toluene) using an acid (e.g., hydrochloric acid, sulfuric acid, phosphoric acid, methanesulfonic acid, p-toluenesulfonic acid, strong acidic ion-exchange resin and the like, preferably hydrochloric acid, sulfuric acid) generally at −30° C. to 100° C., preferably 0° C. to 40° C. generally for 1 min-24 hr, preferably 1 min-5 hr, more preferably 10 min-3 hr.

The amount of the acid to be used for deprotection and cyclization is generally 0.001-10 L, preferably 0.01-2 L, per 1 kg of compound (V). The amount of the solvent to be used for deprotection and cyclization is generally 1-50 L, preferably 2-20 L, per 1 kg of compound (V).

The compound (XIV) can be isolated by any suitable conventional method. For isolation, for example, after completion of the reaction, the reaction mixture is neutralized with an aqueous alkali solution, partitioned, the obtained organic layer is washed with brine, dried over anhydrous magnesium sulfate and the like and the solvent is evaporated. The isolate can be purified by any suitable conventional method.

The compound having a relative configuration represented by the formula (XV) can be produced according to the above-mentioned method using a compound having a relative configuration represented by the formula (XI).

The compound having an absolute configuration represented by the formula (XV) can be produced according to the above-mentioned method using a compound having an absolute configuration represented by the formula (XI). The enantiomer of the compound having an absolute configuration represented by the formula (XV) can be produced according to the above-mentioned method using an enantiomer of the compound having an absolute configuration represented by the formula (XI).

Step (1B)

Production of Compound (IV) from Compound (I)

The compound (IV) can be obtained by protecting the hydroxyl group of compound (I). The reaction for protecting the hydroxyl group varies depending on the kind of the protecting group, and the hydroxyl group of compound (I) can be protected by appropriately determining the reaction conditions and protecting reagent depending on the kind of the protecting group. For example, when hydroxyl group of compound (I) is protected with 1-ethoxyethyl group, compound (I) is reacted with ethyl vinyl ether, which is a protecting reagent, in a solvent (e.g., THF, MTBE, 1,2-dimethoxyethane, 1,4-dioxane, toluene, dichloromethane and the like, preferably THF, MTBE, dichloromethane) in the presence of an acid (e.g., p-toluenesulfonic acid, pyridinium p-toluenesulfonate, methanesulfonic acid, sulfuric acid, boron trifluoride, phosphorus oxychloride, acidic ion-exchange resin and the like, preferably p-toluenesulfonic acid, pyridinium p-toluenesulfonate) generally at −30° C. to 80° C., preferably 0° C. to 40° C. for 10 min-10 hr, preferably 30 min-3 hr.

The amount of the protecting reagent, such as ethyl vinyl ether and the like, to be used is generally 0.8-3 mol, preferably 1-1.5 mol, per 1 mol of compound (I). The amount of the acid to be used is generally 0.00001-0.2 kg, preferably 0.0001-0.1 kg, per 1 kg of compound (I). The amount of the solvent to be used is generally 1-50 L, preferably 3-40 L, per 1 kg of compound (I).

The compound (IV) can be isolated by any suitable conventional method. For isolation, for example, the reaction mixture is neutralized with an aqueous alkali solution, partitioned, the obtained organic layer is washed with aqueous alkali solution, and the solvent is evaporated. The isolate can be purified by any suitable conventional method but may optionally be used in the next reaction without purification.

The compound having a relative configuration represented by the formula (X) can be produced according to the above-mentioned method using a compound having a relative configuration represented by the formula (VII) as a material.

The compound having an absolute configuration represented by the formula (X) can be produced according to the above-mentioned method using a compound having an absolute configuration represented by the formula (VII) as a material. The enantiomer of a compound having an absolute configuration represented by the formula (X) can be produced according to the above-mentioned method using an enantiomer of a compound having an absolute configuration represented by the formula (VII).

Production of Compound (VI) from Compound (IV)

The compound (VI) can be obtained by reducing compound (IV). The reduction reaction can be carried out according to a general method used for reducing lactone to lactol. For example, the reaction can be carried out using a reducing agent (e.g., DIBAL-H, sodium bis-2-methoxyethoxyaluminum hydride, lithium aluminum tri-t-butoxyhydride and the like, preferably DIBAL-H, lithium aluminum tri-t-butoxyhydride) in a solvent (e.g., toluene, THF, MTBE, dichloromethane and the like, preferably toluene, THF) at −100° C. to 50° C., preferably −80° C. to 0° C., for 10 min-6 hr, preferably 15 min-3 hr.

The amount of the reducing agent to be used is generally 0.8-1.5 mol, preferably 1-1.2 mol, per 1 mol of compound (IV). The amount of the solvent to be used is generally 1-50 L, preferably 2-20 L, per 1 kg of compound (IV).

The compound (VI) can be isolated according to any suitable conventional method. For isolation, for example, saturated aqueous ammonium chloride solution is added to the reaction mixture, the mixture is dried over anhydrous magnesium sulfate and the like and filtered, and the solvent is evaporated. The isolate can be purified by any suitable conventional method but may optionally be used in the next reaction without purification.

The compound having a relative configuration represented by the formula (XII) can be produced according to the above-mentioned method using a compound having a relative configuration represented by the formula (X).

The compound having an absolute configuration represented by the formula (XII) can be produced according to the above-mentioned method using a compound having an absolute configuration represented by the formula (X). The enantiomer of a compound having an absolute configuration represented by the formula (XII) can be produced according to the above-mentioned method using an enantiomer of a compound having an absolute configuration represented by the formula (X).

Production of Compound (XIV) from Compound (VI)

The compound (XIV) can be obtained by deprotecting and cyclizing compound (VI). The reaction conditions vary depending on the kind of the protecting groups $P_G$ and $P_{G1}$. For example, when the protecting groups $P_G$ and $P_{G1}$ are a benzyl group and a 1-ethoxyethyl group, respectively, the benzyl group can be removed by reacting compound (VI) in a solvent (e.g., ethyl acetate, acetic acid, ethanol, methanol, THF, methyl isobutyl ketone and the like, preferably ethyl acetate, THF, ethanol) using a catalyst (e.g., Pd/C, Pd(OH)$_2$ and the like, preferably Pd/C) generally at −30° C. to 100° C., preferably 0° C. to 60° C., under a hydrogen atmosphere for 15 min-12 hr, preferably 0.5-6 hr.

The amount of the catalyst to be used for removing benzyl group is generally 0.0001-0.5 kg per 1 kg of compound (VI) and the amount of the solvent to be used is generally 0.5-50 L, preferably 2-20 L, per 1 kg of compound (VI).

After filtering the catalyst, the solvent is evaporated and the obtained reaction mixture is reacted in a solvent (e.g., THF, MTBE, ethyl acetate, ethanol, methanol, methyl isobutyl ketone, toluene and the like, preferably THF, ethanol, methanol) using an acid (e.g., hydrochloric acid, sulfuric acid, methanesulfonic acid, p-toluenesulfonic acid, pyridinium p-toluenesulfonate, acidic ion-exchange resin and the like, preferably hydrochloric acid) generally at −30° C. to 100° C., preferably 0° C. to 60° C. for 10 min-6 hr, preferably 30 min-3 hr, for deprotection of 1-ethoxyethyl group and cyclization.

The amount of the acid to be used for deprotection of 1-ethoxyethyl group and cyclization is generally 0.001-10 L, preferably 0.01-2 L, per 1 kg of compound (VI) and the amount of the solvent to be used is generally 1-50 L, preferably 2-20 L, per 1 kg of compound (VI).

The compound (XIV) can be isolated by any suitable conventional method. For isolation, for example, the reaction mixture is neutralized with a base such as anhydrous potassium carbonate and the like, after which the solvent is evaporated. The isolate can be purified by any suitable conventional method.

The compound having a relative configuration represented by the formula (XV) can be produced according to the above-mentioned method using a compound having a relative configuration represented by the formula (XII).

The compound having an absolute configuration represented by the formula (XV) can be produced according to the above-mentioned method using a compound having an absolute configuration represented by the formula (XII). The enantiomer of a compound having an absolute configuration represented by the formula (XV) can be produced according to the above-mentioned method using an enantiomer of a compound having an absolute configuration represented by the formula (XII).

The present invention further comprises other methods relating to the production of compound (I) and compound (III), which are intermediates for the production method of compound (XIV), from compound (XIII). The methods for producing compound (I) and compound (III) are shown in the following Scheme 3. Particularly, the methods for producing the compounds whose absolute configurations are represented by the formula (VII) and the formula (IX) are shown in Scheme 4. As shown in Scheme 3, the present invention comprises a method for producing compound (XIX) using compound (XIII); a method for producing compound (XX) by hydrolysis of compound (XIX); and a method for producing compound (III) by deprotection of $P_G$ and $R_3$ of compound (XX), followed by acetalization or ketalization and lactonization. The above-mentioned methods of the present invention can be each carried out independently, but it is preferable to combine two or more of the methods.

The method for producing compound (I) comprises hydroxyethylation of compound (XIII) and then cyclization, it is preferable to hydroxyethylate compound (XIII) to form compound (XIX), hydrolyze the compound (XIX) to form compound (XX), and cyclize the compound (XX) to form compound (I). Each method is described in detail in the following.

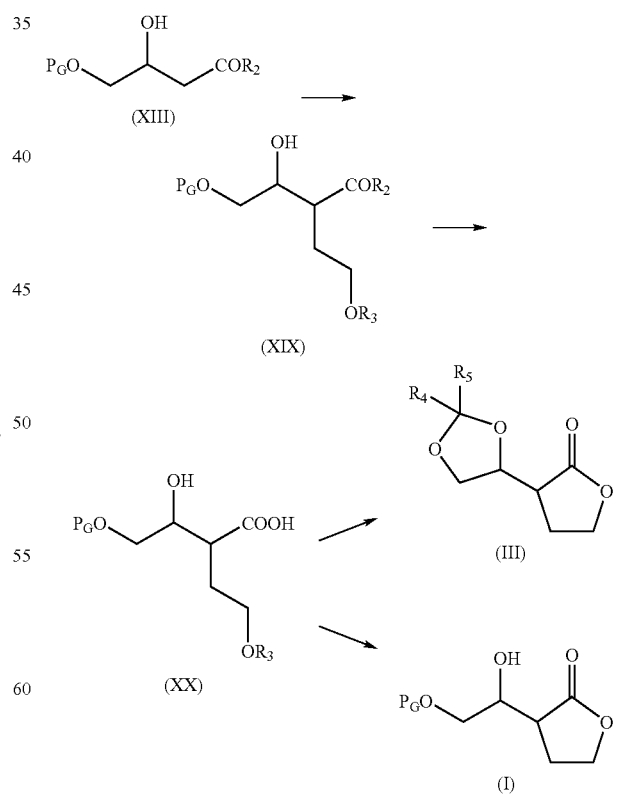

wherein each symbol is as defined above.

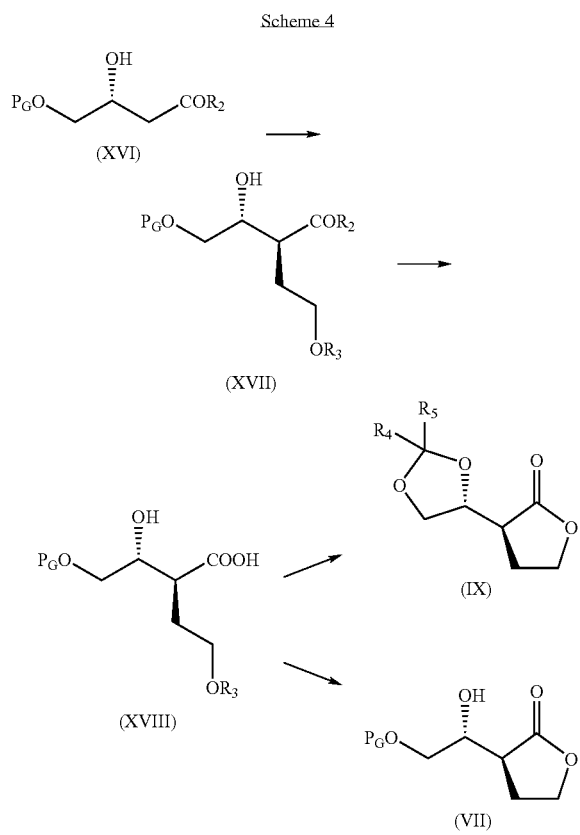

Scheme 4 wherein each symbol is as defined above.

Production of Compound (XIX) from Compound (XIII)

The compound (XIX) can be obtained by hydroxyethylation of (introduction of $R_3O—CH_2CH_2—$ group wherein $R_3$ is as defined above into) compound (XIII). For example, compound (XIII) is reacted with a compound represented by the formula: $R_3O—CH_2CH_2—X$ wherein $R_3$ is as defined above and X is a leaving group, with the addition of a base (e.g., lithium diisopropylamide, lithium dicyclohexylamide, lithium hexamethyldisilazide, sodium hexamethyldisilazide, potassium hexamethyldisilazide and the like, preferably lithium diisopropylamide).

In the formula: $R_3O—CH_2CH_2—X$, as the leaving group X, for example, halogen atom (e.g., iodine atom, bromine atom and the like can be mentioned), methanesulfonyloxy group, trifluoromethanesulfonyloxy group, p-toluenesulfonyloxy group, benzenesulfonyloxy group and the like can be mentioned, and preferably halogen atom, particularly preferably iodine atom, can be mentioned, and as $R_3$, those similar to the examples of the aforementioned compounds (C), (F) and (XVII)-(XX) can be mentioned, and preferably benzyl group and t-butyl group can be mentioned. As the compound represented by the formula: $R_3O—CH_2CH_2—X$, 2-benzyloxyethyl iodide and 2-t-butoxyethyl iodide are preferable.

The amount of the base to be used is generally 0.9-1.5 mol, preferably 1.0-1.3 mol, per 1 mol of compound (XIII).

The amount of the compound represented by the formula: $R_3O—CH_2CH_2—X$ to be used is generally 0.9-2.5 mol, preferably 1.0-1.6 mol, per 1 mol of compound (XIII).

The compound (XIX) is produced in a reaction solvent such as THF, hexane, di-n-butyl ether, MTBE, ethylene glycol dimethyl ether, diethylene glycol dimethyl ether, 1,3-dioxolane, 1,4-dioxane, toluene and the like, preferably THF or hexane. The amount of the reaction solvent to be used is generally 1-100 L, preferably 3-30 L, per 1 kg of compound (XIII).

The reaction temperature is generally −100° C. to 70° C., preferably −80° C. to 40° C., and the reaction time is generally 0.5-48 hr, preferably 3-24 hr.

The compound represented by the formula: $R_3O—CH_2CH_2—X$ can be produced by any suitable known method. For example, 2-benzyloxyethyl iodide can be produced by reacting 2-benzyloxyethanol with methanesulfonyl chloride in the presence of a catalyst such as triethylamine and the like to give 2-benzyloxyethyl methanesulfonate, which is then reacted with sodium iodide, and 2-t-butoxyethyl iodide can be produced using 2-t-butoxyethanol instead of the above-mentioned 2-benzyloxyethanol.

The compound (XIX) can be isolated by any suitable conventional method. For isolation, for example, the reaction mixture is poured into aqueous hydrochloric acid, the mixture is partitioned, the obtained organic layer is washed with aqueous alkali solution, and the solvent is evaporated.

When the above-mentioned method is performed using a compound represented by the formula (XVI), a diastereomer mixture mainly containing a compound having an absolute configuration represented by the formula (XVII) (containing a large amount of anti-form and a small amount of syn-form) can be obtained. When the above-mentioned method is performed using an enantiomer of a compound represented by the formula (XVI), a diastereomer mixture mainly containing an enantiomer of a compound having an absolute configuration represented by the formula (XVII) (containing a large amount of anti-form and a small amount of syn-form) can be obtained.

The diastereomer mixture mainly containing a compound having an absolute configuration represented by the formula (XVII) or a diastereomer mixture mainly containing an enantiomer of a compound having an absolute configuration represented by the formula (XVII) is isolated by HPLC to give a pure compound having an absolute configuration represented by the formula (XVII) or a pure enantiomer of a compound having an absolute configuration represented by the formula (XVII). However, the diastereomer mixture may optionally be subjected to a next reaction without isolation.

Production of Compound (XX) from Compound (XIX)

The compound (XX) can be obtained by hydrolysis of compound (XIX). The hydrolysis is performed by, for example, a reaction of compound (XIX) using a base (e.g., potassium hydroxide, sodium hydroxide, lithium hydroxide and the like, preferably potassium hydroxide) generally at −20° C. to 120° C., preferably 20° C. to 100° C. generally for 0.5-24 hr, preferably 1-12 hr.

The amount of the base to be used for hydrolysis is, for example, generally 1-50 mol, preferably 1.2-10 mol, per 1 mol of compound (XIX), when the base is potassium hydroxide.

Hydrolysis is performed in a reaction solvent such as methanol, ethanol, 2-propanol, water and the like, preferably in a mixed solvent of methanol and water. The amount of the reaction solvent to be used is generally 1-100 L, preferably 5-50 L, per 1 kg of compound (XIX).

The compound (XX) can be isolated according to any suitable conventional method. For isolation, for example, after hydrolysis, the reaction mixture is adjusted to generally pH 0-7, preferably pH 0.1-3, using an acid (e.g., hydrochloric acid, sulfuric acid, phosphoric acid and the like, preferably hydrochloric acid), the solution is partitioned, the obtained organic layer is washed with saturated brine, and the solvent is evaporated.

When the above-mentioned method is performed using the diastereomer mixture mainly containing a compound having an absolute configuration represented by the formula (XVII) (containing a large amount of anti-form and a small amount of syn-form), a diastereomer mixture mainly containing a compound having an absolute configuration represented by the formula (XVIII) (containing a large amount of anti-form and a small amount of syn-form) can be obtained. When the above-mentioned method is performed using the diastereomer mixture mainly containing an enantiomer of a compound having an absolute configuration represented by the formula (XVII) (containing a large amount of anti-form and a small amount of syn-form), a diastereomer mixture mainly containing an enantiomer of a compound having an absolute configuration represented by the formula (XVIII) (containing a large amount of anti-form and a small amount of syn-form) can be obtained.

When the product from the hydrolysis is obtained as a diastereomer mixture, the purity is further increased by adding organic amine after hydrolysis to give an organic amine salt of compound (XX) and recrystallizing the salt.

As the organic amine, dibenzylamine, benzylamine, dicyclohexylamine, cyclohexylamine, aniline, diethylamine, diisopropylamine, (S)-phenethylamine and the like can be mentioned, with preference given to dibenzylamine. The amount of the organic amine to be used is generally 0.5-1.5 mol, preferably 0.8-1.3 mol, per 1 mol of compound (XX). An organic amine salt is formed in a reaction solvent such as ethanol, methanol, 2-propanol, 1-propanol, t-butyl alcohol, MTBE, diisopropyl ether, methyl isobutyl ketone, ethyl acetate, water and the like, preferably ethanol. The amount of the reaction solvent to be used is generally 1-100 L, preferably 3-30 L, per 1 kg of compound (XX).

The organic amine salt can be produced by heating to generally 20° C. to 100° C., preferably 40° C. to 80° C., and then cooling to generally −20° C. to 40° C., preferably −10° C. to 25° C.

The solvent to be used for the recrystallization of the obtained organic amine salt is, for example, ethanol, methanol, 2-propanol, 1-propanol, ethyl acetate, diisopropyl ether, water and the like, preferably ethanol. The amount of the solvent to be used is generally 1-100 L, preferably 3-30 L, per 1 kg of organic amine salt.

A free compound (XX) can be obtained by any suitable conventional method. For example, a reaction mixture of the obtained organic amine salt of compound (XX) is adjusted to generally pH 0-7, preferably pH 0.5-4, using an acid (e.g., hydrochloric acid, sulfuric acid, phosphoric acid and the like, preferably hydrochloric acid), the mixture is partitioned, the obtained organic layer is washed with saturated brine, and the solvent is evaporated.

By forming a salt of a diastereomer mixture mainly containing a compound having an absolute configuration represented by the formula (XVIII) (i.e., containing a large amount of anti-form and a small amount of syn-form) with an organic amine, a compound having an absolute configuration represented by the formula (XVIII) and a salt thereof can be stereoselectively obtained with a superior optical and configurational purity. By forming a salt of a diastereomer mixture mainly containing an enantiomer of a compound having an absolute configuration represented by the formula (XVIII) (i.e., containing a large amount of anti-form and a small amount of syn-form) with an organic amine, an enantiomer of a compound having an absolute configuration represented by the formula (XVIII) and a salt thereof can be stereoselectively obtained with a superior optical and configurational purity.

Production of Compound (III) from Compound (XX)

The compound (III) can be obtained by deprotection of $P_G$ and $R_3$ of compound (XX), followed by lactonization, and acetalization or ketalization thereof. These steps may be performed separately but are preferably performed simultaneously for convenience. When compound (III) is obtained, for example, by simultaneous deprotection, lactonization, and acetalization or ketalization of $P_G$ and $R_3$ of compound (XX) the reaction is carried out with the addition of an acetalization reagent or a ketalization reagent (i.e., diol-protecting reagent) using a catalyst (e.g., in the co-presence of an acid catalyst such as a strong acidic cation ion-exchange resin (Amberlyst 15 (Dry)), phosphoric acid, sulfuric acid, hydrochloric acid and the like, and a reduction catalyst such as palladium-carbon, palladium hydroxide and the like, with preference given to the presence of a combination of a strong acidic cation ion-exchange resin (Amberlyst 15 (Dry)) and palladium-carbon) under a hydrogen atmosphere by preferably adding a dehydrating agent such as anhydrous magnesium sulfate and the like generally at −20° C. to 100° C., preferably 0° C. to 60° C., generally for 0.5-24 hr, preferably 1-12 hr.

The acetalization reagent and the ketalization reagent (diol-protecting reagent) vary depending on the kinds of $R_4$ and $R_5$ which are protecting group constituent elements. For example, when both $R_4$ and $R_5$ are methyl groups, 2,2-dimethoxypropane or acetone can be used.

The amount of the acetalization reagent or the ketalization reagent, such as 2,2-dimethoxypropane and the like, is generally 1-30 mol, preferably 1-10 mol, per 1 mol of compound (XX). The amount of the catalyst to be used is generally 0.1-500 g, preferably 1-250 g, per 1 kg of compound (XX), for both the acid catalyst and the reduction catalyst. This reaction can be carried out using a solvent (e.g., toluene, THF, dichloromethane etc.) or without using a solvent. When a solvent is used, the amount of the solvent to be used is generally 1-50 L, preferably 3-30 L, per 1 kg of compound (XX).

The compound (III) can be isolated according to any suitable conventional method. For isolation, for example, the reaction mixture is filtered, the solvent is evaporated, an aqueous alkali solution is poured, the mixture is partitioned, and the solvent is evaporated from the obtained organic layer.

By performing the above-mentioned method using a compound having an absolute configuration represented by the formula (XVIII), a compound having an absolute configuration represented by the formula (IX) can be stereoselectively obtained at a superior optical purity. In addition, for example, by performing the aforementioned production method of compound (V) from compound (III) using the compound having an absolute configuration represented by the formula (IX), a compound having an absolute configuration represented by the formula (XI) can be stereoselectively obtained at a superior optical purity, and moreover, for example, by performing the aforementioned production method of compound (XIV) from compound (V) using the obtained compound having an absolute configuration represented by the formula (XI), a compound having an absolute configuration represented by the formula (XV) can be stereoselectively obtained at a superior optical purity. In addition, by performing the above-mentioned production method using an enantiomer of a compound having an absolute configuration represented by the formula (XVIII), an enantiomer of a compound having an absolute configuration represented by the formula (IX), an enantiomer of a compound having an absolute configuration represented by the formula (XI) and an enantiomer of a compound having an absolute configuration represented by the formula (XV) can be stereoselectively obtained at superior optical purities.

Production of Compound (I) from Compound (XX)

The compound (I) can be obtained by cyclization of compound (XX). To be specific, compound (I) can be obtained by lactonization after deprotection of $R_3$ of compound (XX). These steps may be performed separately but are preferably performed simultaneously for convenience. When compound (I) is obtained by simultaneous deprotection of $R_3$ and lactonization, for example, the reaction is carried out with the addition of an acid (e.g., trifluoromethanesulfonic acid, methanesulfonic acid and the like, preferably trifluoromethanesulfonic acid).

The amount of the acid to be used is generally 0.0005-0.5 mol, preferably 0.05-0.5 mol, per 1 mol of compound (XX).

The compound (I) is produced in a reaction solvent such as THF, 1,2-dimethoxyethane, MTBE and the like, preferably THF. The amount of the reaction solvent to be used is generally 1-100 L, preferably 3-30 L, per 1 kg of compound (XX).

The reaction temperature is generally −30° C. to 100° C., preferably 0° C. to 60° C., and the reaction time is generally 0.5-96 hr, preferably 3-72 hr.

The compound (I) can be isolated according to any suitable conventional method. For isolation, for example, after evaporation of the solvent of the reaction mixture, aqueous alkali solution is poured, the mixture is partitioned, the obtained organic layer is washed with saturated brine, and the solvent is evaporated.

By performing the above-mentioned method using a compound having an absolute configuration represented by the formula (XVIII), a compound having an absolute configuration represented by the formula (VII) can be stereoselectively obtained at a superior optical purity. In addition, by performing the above-mentioned method using an enantiomer of a compound having an absolute configuration represented by the formula (XVIII), an enantiomer of a compound having an absolute configuration represented by the formula (VII) can be stereoselectively obtained at a superior optical purity.

The present invention additionally comprises methods for producing the compound (XV) comprising (1) using compound (XXI) as a starting material to produce compound (XXII), (2) using compound (XXII) to produce compound (XXIV) and compound (XXV) to produce compound (XXVI), and (3) inverting compound (XXVI) to form compound (XV). That is, the present invention is characterized by a method for producing compound (XXII) comprising stereoselectively reducing compound (XXI); a method for producing compound (XXIV) comprising (2A) simultaneous deprotection and introduction of protecting group of compound (XXII) to form the compound (XXIV), or (2B) deprotection of compound (XXII) to form compound (XXIII) and introduction of protecting group into the compound (XXIII) to form compound (XXIV); a method for producing compound (XXV) comprising reducing compound (XXIV); a method for producing compound (XXVI) comprising deprotecting and cyclizing compound (XXV); and a method for producing compound (XV) comprising inverting the hydroxyl group of compound (XXVI). The above-mentioned methods of the present invention can be each performed independently, but it is more preferable to combine two or more of the methods.

(1) Production of Compound (XXII) from Compound (XXI)

The compound (XXI) can be obtained by a known method (e.g., method described in JP-A-10-218881 etc.).

The compound (XXII) can be obtained by stereoselective reduction of compound (XXI).

As the method of stereoselective reduction, various stereoselective reduction reactions can be applied, but generally, asymmetric hydrogenation reaction using a transition metal catalyst having an asymmetric ligand is preferable, because it shows a high asymmetric yield, the number of catalyst rotations is large and the like.

Asymmetric hydrogenation reaction using a transition metal catalyst having an asymmetric ligand is explained in detail in the following.

The compound (XXII) can be produced by, for example, reacting compound (XXI) with hydrogen in a solvent in the presence of a transition metal catalyst having an asymmetric ligand.

As the asymmetric ligand, for example, optically active phosphine derivative, optically active diamine derivative, optically active amino alcohol derivative, optically active bisoxazoline derivative, optically active salen derivative and the like can be mentioned. Generally, however, an optically active phosphine derivative is preferable because it shows a high asymmetric yield, and the number of catalyst rotations is large and the like.

As the optically active phosphine derivative, for example, compound (L1)-compound (L6), enantiomers thereof and the like can be mentioned. Of these, compound (L1) and an enantiomer thereof are preferable, and compound (L1) and an enantiomer thereof, wherein Ra and Rb are phenyl groups and Rc is a hydrogen atom, i.e., optically active BINAP (optically active 2,2′-bis(diphenylphosphino)-1,1′-binaphthyl), more precisely, (S)-BINAP and (R)-BINAP which is an enantiomer thereof, are more preferable, because they can be synthesized easily and can be obtained easily and the like.

In the formulas (L1)-(L6), as the substituents for the optionally substituted phenyl, which are represented by Ra, Rb, Rd, Re, Rh, Ri, Rj, Rk, Rl, Rm, Rn and Ro, for example, halogen atom, alkyl, alkoxy and the like can be mentioned, and halogen atom, alkyl and the like can be preferably mentioned. The number of the substituents is not particularly limited, but it is preferably 1-3, which substituents may be the same or different.

In the formulas (L1)-(L6), as the substituents for the optionally substituted cyclohexyl, which are represented by Ra, Rb, Rd, Re, Rh, Ri, Rj, Rk, Rl, Rm, Rn and Ro, alkyl (e.g., methyl, ethyl, isopropyl, tert-butyl and the like) and the like can be mentioned, and methyl, tert-butyl and the like can be preferably mentioned. The number of the substituents is not particularly limited, but it is preferably 1-3, which substituents may be the same or different.

Of the substituents, halogen atom is exemplified by fluorine atom, chlorine atom, bromine atom and iodine atom, with preference given to chlorine atom and bromine atom.

Of the substituents, alkyl is preferably a straight chain or branched chain alkyl preferably having 1 to 6, more preferably 1 to 4, carbon atoms, such as methyl, ethyl, propyl, isopropyl, butyl, isobutyl, sec-butyl, tert-butyl, pentyl, isopentyl, neopentyl, hexyl, isohexyl and the like, with preference given to methyl, tert-butyl and the like.

Of the substituents, alkoxy is a straight chain or branched chain alkoxy preferably having 1 to 6, more preferably 1 to 4, carbon atoms, such as methoxy, ethoxy, propoxy, isopropoxy, butoxy, isobutoxy, sec-butoxy, tert-butoxy, pentoxy, isopentoxy, neopentoxy, hexyloxy, isohexyloxy and the like, with preference given to methoxy, tert-butoxy and the like.

In the formulas (L1) and (L2), as the halogen atom represented by Rc, Rf and Rg, those mentioned for halogen atom as the above-mentioned substituent can be mentioned, with preference given to chlorine atom and bromine atom.

In the formulas (L1) and (L2), as alkyl represented by Rc, Rf and Rg, a straight chain or branched chain alkyl preferably having 1 to 6, more preferably 1 to 4, carbon atoms, such as methyl, ethyl, propyl, isopropyl, butyl, isobutyl, sec-butyl, tert-butyl, pentyl, isopentyl, neopentyl, hexyl, isohexyl and the like can be mentioned, with preference given to methyl, tert-butyl and the like.

In the formulas (L1) and (L2), as alkoxy represented by Rc, Rf or Rg, a straight chain or branched chain alkoxy preferably having 1 to 6, more preferably 1 to 4, carbon atoms, such as methoxy, ethoxy, propoxy, isopropoxy, butoxy, isobutoxy, sec-butoxy, tert-butoxy, pentoxy, isopentoxy, neopentoxy, hexyloxy, isohexyloxy and the like can be mentioned, with preference given to methoxy, tert-butoxy and the like.

In the formulas (L1) and (L2), as the substituent for the optionally substituted phenyl for Rc, Rf or Rg, those similar to the substituents of the "optionally substituted phenyl" for the above-mentioned Ra and the like can be mentioned, with preference given to methyl, tert-butyl and the like. The number of the substituents is not particularly limited, but it is preferably 1-3, which substituents may be the same or different.

The transition metal of the transition metal catalyst is not particularly limited, and, for example, Group VIII transition metals such as ruthenium, rhodium, palladium, iridium, platinum and the like are preferable, and ruthenium is particularly preferable.

The transition metal catalyst may be one wherein the one kind of asymmetric ligand is coordinated with one transition metal or may be two or more asymmetric ligands are simultaneously coordinated with one transition metal.

The preparation method of a transition metal catalyst having an asymmetric ligand is not particularly limited. For example, a transition metal complex formed from an optically active phosphine derivative and ruthenium can be mentioned, which is a preferable transition metal catalyst (hereinafter to be also referred to as a phosphine-ruthenium complex) prepared according to a known method, such as a method described in J. Chem. Soc., Chem. Commun., 922 (1985). To be specific, a ruthenium salt or a complex thereof (e.g., benzene ruthenium(II) chloride dimer, dichloro(1,5-cyclooctadiene)ruthenium (II) polymer etc.) is reacted with an optically active phosphine derivative in a solvent to give a phosphine-ruthenium complex. In addition, a ruthenium salt or a complex thereof and an optically active phosphine derivative are directly added to a reaction solvent for the reduction reaction to allow for preparation of a phosphine-ruthenium complex simultaneously with reduction reaction.

The proportion of the asymmetric ligand and the transition metal is 0.3-3 mol, preferably 0.5-2 mol, of the transition metal to 1 mol of the asymmetric ligand.

The amount of the transition metal catalyst having an asymmetric ligand to be used is generally 0.00001-0.2 mol, preferably 0.0001-0.1 mol, per 1 mol of compound (XXI).

The pressure of hydrogen to be used is generally 0.1-10 MPa, preferably 0.3-3 MPa.

As the solvent of the reduction reaction, for example, ethanol, methanol, 2-propanol, 1-propanol, ethyl acetate, acetic acid, DMF and the like, preferably ethanol, 1-propanol and the like, can be mentioned. The amount of the solvent to be used is generally 1-30 L, preferably 3-15 L, per 1 kg of compound (XXI).

The reaction temperature of the reduction reaction is generally 0° C. to 150° C., preferably 50° C. to 120° C. While the reaction time depends on the reagent to be used, reaction temperature, pressure of hydrogen and the like, the reaction generally ends in 1-24 hr.

The compound (XXII) can be isolated by any suitable conventional method, and, for example, compound (XXII) can be isolated by pouring the reaction mixture into an aqueous sodium hydrogen carbonate solution, extracting the mixture with a solvent, partitioning the mixture, washing the organic layer and removing the catalyst by flash chromatography and the like. The isolate can be purified by any suitable conventional method but may optionally be used in the next reaction without purification.

In the production method of the present invention, a compound having an absolute configuration represented by the formula (XXII), and an enantiomer thereof can be produced by selecting the asymmetric ligand. Generally, for example, when compound (L1)-compound (L6) are used as asymmetric ligands, a compound having an absolute configuration represented by the formula (XXII), i.e., (1'R,2R)-form, can be produced, and when an enantiomer of compound (L1)-compound (L6) is used as an asymmetric ligand, an enantiomer of a compound having an absolute configuration represented by the formula (XXII), i.e., (1'S,2S)-form, can be produced. To be specific, for example, when optically active BINAP is used as an asymmetric ligand, a compound having an absolute configuration represented by the formula (XXII), i.e., (1'R, 2R)-form, can be produced by the use of (S)-BINAP, and an enantiomer of a compound having an absolute configuration represented by the formula (XXII), i.e., (1'S,2S)-form, can be produced by the use of (R)-BINAP.

(2) Production of Compound (XXVI) from Compound (XXII)

The compound (XXVI) can be obtained by introducing a protecting group into compound (XXII), followed by reduction and cyclization. That is, a protecting group is introduced into compound (XXII) to form compound (XXIV), and the compound (XXIV) is reduced to form compound (XXV), and the compound (XXV) is deprotected and cyclized to form compound (XXVI).

Production of Compound (XXIV) from Compound (XXII)

The compound (XXIV) can be produced using compound (XXII) by a process comprising, for example, (2A) deprotecting the hydroxyl group of compound (XXII) and simultaneous introduction of a protecting group of diol to directly form compound (XXIV), or (2B) deprotecting compound (XXII) to form compound (XXIII), introduction of a protecting group of diol into the obtained compound (XXIII) to form compound (XXIV) and the like. Of these, step (2A) is convenient and preferable.

The method for obtaining compound (XXIV) by simultaneous deprotection of compound (XXII) and protection of diol is explained in the following. This method can be performed by simultaneous addition of a deprotecting reagent and a protecting reagent, wherein the reagent is appropriately determined according to the group to be deprotected and the kind of the protecting group of diol.

As a non-limiting example, When the protecting group of compound (XXII) is a benzyl group and the diol-protecting group is a dimethylmethylene group, compound (XXII) and 2,2-dimethoxypropane and/or acetone, which are protecting reagents, are reacted in a solvent (e.g., THF, ethyl acetate and the like, preferably THF etc.) or without a solvent using a catalyst (e.g., Pd/C, Pd(OH)$_2$ and the like, preferably Pd/C etc.) and an acidic ion-exchange resin (e.g., Amberlyst 15E (manufactured by Rohm & Haas), Nafion SAC13 (manufactured by Dupont) etc.) or an acid (e.g., phosphoric acid, hydrochloric acid, sulfuric acid, methanesulfonic acid, trifluoromethanesulfonic acid, p-toluenesulfonic acid, benzenesulfonic acid, boron trifluoride, phosphorus oxychloride etc.) generally at −20° C. to 100° C., preferably 0° C. to 50° C., under a hydrogen atmosphere generally for 0.5-48 hr, preferably 1-24 hr, to give compound (XXIV).

The amount of the protecting reagent such as 2,2-dimethoxypropane and the like is generally 0.5-100 L, preferably 1-50 L, per 1 kg of compound (XXII). The amount of the reduction catalyst to be used is generally 0.0001-0.5 kg per 1 kg of compound (XXII). The amount of the acidic ion-exchange resin to be used is generally 0.001-0.5 kg, preferably 0.005-0.1 kg, per 1 kg of compound (XXII). When other acid is used, the amount of the acid to be used is generally 0.00001-0.1 kg, preferably 0.0001-0.01 kg, per 1 kg of compound (XXII). When a solvent is used, the amount of the solvent to be used is generally 0.5-50 L, preferably 1-25 L, per 1 kg of compound (XXII).

The compound (XXIV) can be isolated by filtering off the catalyst and evaporating the solvent. The isolate can be purified by any suitable conventional method but may optionally be used in the next reaction without purification.

When $R_{10}$ is a hydrogen atom and $R_{11}$ is a lower alkyl group or a phenyl group, which are the constituent elements of the protecting group, the reaction can be carried out in the same manner as in the above, using alkanal or benzaldehyde and/or acetal of alkanal or benzaldehyde (e.g., dimethyl acetal etc.) instead of the above-mentioned 2,2-dimethoxypropane or acetone.

When $R_{10}$ is a lower alkyl group or a phenyl group and $R_{11}$ is a lower alkyl group or a phenyl group, the reaction can be generally carried out in the same manner as in the above, using $R_{10}COR_{11}$ and/or acetal thereof (e.g., dimethyl acetal etc.) instead of the above-mentioned 2,2-dimethoxypropane or acetone.

When $R_{10}$ is a lower alkyl group or a phenyl group and $R_{11}$ is a lower alkoxyl group, the reaction can be carried out in the same manner as in the above, using trialkyl orthoalkanoate (e.g., MeC(OEt)$_3$ etc.) or trialkyl orthobenzoate instead of the above-mentioned 2,2-dimethoxypropane or acetone.

When $R_{10}$ is a hydrogen atom and $R_{11}$ is a lower alkoxyl group, the reaction can be carried out in the same manner as in the above, using trialkyl orthoformate instead of the above-mentioned 2,2-dimethoxypropane or acetone.

When $R_{10}$ and $R_{11}$ are lower alkoxyl groups, the reaction can be carried out in the same manner as in the above, using tetraalkyl orthocarbonate instead of the above-mentioned 2,2-dimethoxypropane or acetone.

The compound having an absolute configuration represented by the formula (XXIV) can be produced according to the above-mentioned method, using a compound having an absolute configuration represented by the formula (XXII). The enantiomer of the compound having an absolute configuration represented by the formula (XXIV) can be produced according to the above-mentioned method, using an enantiomer of a compound having an absolute configuration represented by the formula (XXII).

Production of Compound (XXV) from Compound (XXIV)

The compound (XXV) can be obtained by reducing compound (XXIV). The reduction reaction can be carried out according to a method generally used for reducing lactone to lactol. For example, the reaction is carried out using a reducing agent (e.g., DIBAL-H, sodium bis-2-methoxyethoxyaluminum hydride, lithium aluminum tri-t-butoxyhydride and the like, preferably DIBAL-H, lithium aluminum tri-t-butoxyhydride etc.) in a solvent (e.g., dichloromethane, toluene, THF, MTBE and the like, preferably dichloromethane, toluene, THF etc.) at −100° C. to 50° C., preferably −80° C. to 0° C., for 10 min-6 hr, preferably 15 min-3.5 hr.

The amount of the reducing agent to be used is generally 0.8-1.5 mol, preferably 1-1.2 mol, per 1 mol of compound (XXIV). The amount of the solvent to be used is generally 1-50 L, preferably 2-20 L, per 1 kg of compound (XXIV).

The compound (XXV) can be isolated according to any suitable conventional method. For isolation, for example, a reaction mixture is poured into saturated aqueous ammonium chloride solution, the mixture is partitioned and the obtained organic layer is dried over anhydrous magnesium sulfate and the like and filtered, and the solvent is evaporated. The isolate can be purified by any suitable conventional method but may optionally be used in the next reaction without purification.

The compound having an absolute configuration represented by the formula (XXV) can be produced according to the above-mentioned method using a compound having an absolute configuration represented by the formula (XXIV). The enantiomer of a compound having an absolute configuration represented by the formula (XXV) can be produced according to the above-mentioned method using an enantiomer of a compound having an absolute configuration represented by the formula (XXIV).

Production of Compound (XXVI) from Compound (XXV)

The compound (XXVI) can be obtained by deprotecting and cyclizing compound (XXV). For example, compound (XXV) can be deprotected and cyclized by a reaction in a solvent (e.g., THF, 1,4-dioxane, MTBE, di-n-butyl ether, 1,2-dimethoxyethane, toluene and the like, preferably THF, toluene etc.) using an acid (e.g., hydrochloric acid, sulfuric acid, phosphoric acid, methanesulfonic acid, p-toluenesulfonic acid, strong acidic ion-exchange resin and the like, preferably hydrochloric acid, sulfuric acid etc.) generally at −30° C. to 100° C., preferably 0° C. to 40° C., generally for 1 min-48 hr, preferably 1 min-24 hr, more preferably 10 min-16 hr.

The amount of the acid to be used for deprotection and cyclization is generally 0.001-10 L, preferably 0.01-2 L, per 1 kg of compound (XXV). The amount of the solvent to be used for deprotection and cyclization is generally 1-50 L, preferably 2-20 L, per 1 kg of compound (XXV).

The compound (XXVI) can be isolated by any suitable conventional method. For isolation, for example, after completion of the reaction, the reaction mixture is neutralized with an aqueous alkali solution and partitioned, the obtained organic layer is washed with brine and dried over anhydrous magnesium sulfate and the like, and the solvent is evaporated. The isolate can be further purified by any suitable conventional method but may optionally be used in the next reaction without purification.

The compound having an absolute configuration represented by the formula (XXVI) can be produced according to the above-mentioned method using a compound having an absolute configuration represented by the formula (XXV). The enantiomer of the compound having an absolute configuration represented by the formula (XXVI) can be produced according to the above-mentioned method using an enantiomer of the compound having an absolute configuration represented by the formula (XXV).

(3) Production of Compound (XV) from Compound (XXVI)

The compound (XV) can be obtained by inverting the hydroxyl group of compound (XXVI). The hydroxyl group can be inverted by a process comprising, for example, (2C) oxidizing compound (XXVI) to compound (XXVII) and reducing the compound to form compound (XV), or (2D)

inversion esterification to directly convert compound (XXVI) to compound (XXVIII) and hydrolysis to form compound (XV) and the like.

Step (2C)

Production of Compound (XXVII) from Compound (XXVI)

The compound (XXVII) can be obtained by oxidizing compound (XXVI).

The oxidation reaction can be carried out according to any suitable conventional method used for oxidation of alcohol to ketone. For example, the reaction is carried out using oxalyl chloride and dimethyl sulfoxide in the presence of a base such as triethylamine and the like in a solvent (e.g., methylene chloride, chlorobenzene, ethyl acetate, tert-butyl alcohol and the like, preferably methylene chloride etc.) at −100° C. to 50° C., preferably −80° C. to 0° C. for 10 min-12 hr, preferably 30 min-5 hr.

The amount of oxalyl chloride to be used is generally 1-4 mol, preferably 1.5-3 mol, per 1 mol of compound (XXVI). The amount of dimethyl sulfoxide to be used is generally 1-5 mol, preferably 2-4 mol, per 1 mol of compound (XXVI). The amount of the solvent to be used is generally 1-100 L, preferably 5-50 L, per 1 kg of compound (XXVI). The amount of the base, such as triethylamine and the like, to be used is generally 3-30 mol, preferably 5-20 mol, per 1 mol of compound (XXVI).

The compound (XXVII) can be isolated according to any suitable conventional method. For isolation, for example, the reaction mixture is poured into saturated aqueous ammonium chloride solution, the mixture is partitioned, the obtained organic layer is washed with saturated aqueous ammonium chloride solution, and the solvent is evaporated. The isolate can be purified by any suitable conventional method but may optionally be used in the next reaction without purification.

Production of Compound (XV) from Compound (XXVII)

The compound (XV) can be obtained by reducing compound (XXVII).

The reduction reaction can be carried out by any suitable conventional method used for reducing ketone into alcohol. For example, the reaction can be carried out using a reducing agent (e.g., lithium aluminum hydride, sodium borohydride, lithium borohydride, DIBAL-H and the like, preferably lithium aluminum hydride, sodium borohydride etc.) in a solvent (e.g., THF, MTBE, methanol, ethanol, 2-propanol and the like, preferably THF, methanol, ethanol etc.) at −30° C. to 100° C., preferably 0° C. to 50° C. for 10 min-12 hr, preferably 30 min-5 hr.

The amount of the reducing agent to be used is generally 0.25-1.5 mol, preferably 0.25-0.75 mol, per 1 mol of compound (XXVII). The amount of the solvent to be used is generally 2-100 L, preferably 5-50 L, per 1 kg of compound (XXVII).

The compound (XV) can be isolated according to any suitable conventional method. For isolation, for example, aqueous sodium hydroxide solution is added to the reaction mixture, the mixture is filtered, washed with THF, the filtrate is dried over anhydrous magnesium sulfate and the like and filtered, and the solvent is evaporated. The separated product can be purified by any suitable conventional method.

Step (2D)

Production of Compound (XXVIII) from Compound (XXVI)

The compound (XXVIII) can be obtained by inversion esterification of hydroxyl group of compound (XXVI). The inversion esterification is conducted by a reaction of, for example, compound (XXVI) with a compound represented by the formula: $R_9OH$, wherein $R_9$ is as defined above, in the presence of a condensation agent such as triphenylphosphine or trialkylphosphine (e.g., tricyclohexylphosphine, tributylphosphine, trihexylphosphine, trioctylphosphine and the like, preferably triphenylphosphine, tricyclohexylphosphine etc.) and azodicarboxylic acid ester (e.g., diethyl azodicarboxylate, diisopropyl azodicarboxylate, tert-butyl azodicarboxylate, dimethyl azodicarboxylate, dibenzyl azodicarboxylate and the like, preferably diethyl azodicarboxylate, diisopropyl azodicarboxylate etc.) or azodicarboxylic amide (e.g., 1,1'-azobis(N,N-dimethylformamide), 1,1'-(azodicarbonyl)dipiperidine and the like, preferably 1,1'-(azodicarbonyl)dipiperidine etc.). For example, the reaction can be carried out using a condensation agent in a solvent (e.g., toluene, xylene, mesitylene, THF, MTBE, 1,2-dimethoxyethane, dichloromethane, chlorobenzene and the like, preferably toluene, xylene, THF etc.) at −20° C. to 100° C., preferably 0° C. to 60° C. for 0.5-48 hr, preferably 2-24 hr.

As the compound represented by the formula: $R_9OH$, for example, benzoic acid, 4-methoxybenzoic acid, 4-nitrobenzoic acid, 3,5-dinitrobenzoic acid, 4-phenylbenzoic acid, acetic acid, formic acid, trifluoroacetic acid and the like, preferably benzoic acid, acetic acid and the like, can be mentioned. The amount of the compound represented by the formula: $R_9OH$ to be used is generally 1-4 mol, preferably 1-2.5 mol, per 1 mol of compound (XXVI). The amount of the solvent to be used is generally 2-100 L, preferably 5-50 L, per 1 kg of compound (XXVI).

The amount of triphenylphosphine or trialkylphosphine to be used is generally 1-4 mol, preferably 1-2.5 mol, per 1 mol of compound (XXVI). The amount of azodicarboxylic acid ester or azodicarboxylic amide to be used is generally 1-4 mol, preferably 1-2.5 mol, per 1 mol of compound (XXVI).

The compound (XXVIII) can be isolated according to any suitable conventional method. For isolation, for example, the reaction mixture is partitioned, the obtained organic layer is washed with water and the solvent is evaporated. The isolate can be purified by any suitable conventional method but may optionally be used in the next reaction without purification.

Production of Compound (XV) from Compound (XXVIII)

The compound (XV) can be obtained by hydrolysis of compound (XXVIII).

The hydrolysis can be performed by any suitable conventional method using, for example, a base. The reaction is carried out in the presence of a base (e.g., sodium hydroxide, potassium hydroxide, lithium hydroxide, potassium carbonate, ammonia and the like, preferably sodium hydroxide, potassium carbonate etc.) in a solvent (e.g., methanol, ethanol, 2-propanol, water, or a mixed solvent thereof and the like, preferably methanol, ethanol, a mixed solvent of methanol and water, a mixed solvent of ethanol and water, etc.) at 0° C. to 80° C., preferably 10° C. to 50° C. for 10 min-24 hr, preferably 0.5 hr-12 hr.

The amount of the base to be used is generally 1-200 mol, preferably 2-130 mol, per 1 mol of compound (XXVIII). The amount of the solvent to be used is generally 1-1000 L, preferably 5-500 L, per 1 kg of compound (XXVIII).

The compound (XV) can be isolated according to any suitable conventional method. For isolation, for example, the solvent of the reaction mixture is evaporated, water is added to the residue, the aqueous layer is washed with toluene, added with sodium chloride to allow saturation, the mixture is partitioned, the organic layer is dried over anhydrous magnesium sulfate and the like, and the solvent is evaporated. The isolate can be purified by any suitable conventional method.

The compound having an absolute configuration represented by the formula (XV) can be produced according to the method of step (2C) or (2D) using a compound having an absolute configuration represented by the formula (XXVI). An enantiomer of the compound having an absolute configuration represented by the formula (XV) can be produced according to the method of step (2C) or (2D) using an enantiomer of a compound having an absolute configuration represented by the formula (XXVI).

EXAMPLES

The present invention is explained in detail by referring to Examples, which are not to be construed as limitative, wherein * shows a relative configuration and (±) shows a racemate.

Example 1 Synthesis of (1'R*,2S*)-2-[2'-(1,1-dimethylethoxy)-1'-hydroxyethyl]-4-butanolide Compound Having a Relative Configuration Represented by the Formula (VII)

Ethyl 4-t-butoxyacetoacetate (20.0 g) synthesized according to the method described in Heterocycles 26, 2841 (1987) was dissolved in methanol (150 mL) and sodium borohydride (1.68 g) was added at a temperature of from 5° C. to 15° C. The mixture was stirred for 1 hr and water (100 mL) was added. The solvent was mostly evaporated, and the organic layer extracted twice with MTBE (150 mL) was washed well with water. MTBE was evaporated to give ethyl (±)-4-t-butoxy-3-hydroxybutanoate (16.9 g). To a solution of lithium diisopropylamide 1.5 M cyclohexane solution (73 mL) in THF (100 mL) was added a solution of ethyl (±)-4-t-butoxy-3-hydroxybutanoate (10.66 g) in THF (30 mL) at a temperature of from −58° C. to −48° C. and the temperature was raised to −20° C. Separately, 2-iodoethanol (21.5 g) and ethyl vinyl ether (11.4 g) were mixed in the presence of p-toluenesulfonic acid monohydrate (10 mg) to give 2-(1-ethoxyethoxy)ethyl iodide (19.1 g) and 15.3 g thereof was added dropwise at a temperature near −20° C. to 0° C. The mixture was stirred overnight at room temperature. The reaction mixture was poured into a 1N aqueous hydrochloric acid (100 mL), MTBE (100 mL) was added and the mixture was extracted and washed with saturated aqueous sodium hydrogen carbonate solution. The solvent was evaporated and ethanol (150 mL) and p-toluenesulfonic acid monohydrate (1.3 g) were added to the residue. The mixture was stirred at room temperature for 6 hr. Saturated aqueous sodium hydrogen carbonate solution (20 mL) was added to the reaction mixture and the solvent was mostly evaporated. The residue was extracted with MTBE (100 mL). The organic layer was washed with saturated aqueous sodium hydrogen carbonate solution (50 mL) and dried over anhydrous magnesium sulfate. The solvent was evaporated and the residue was subjected to flash chromatography using heptane/ethyl acetate (3:1) as an eluent to give the title compound (2.0 g) as pale yellow crystals.

$^1$H-NMR (CDCl$_3$, δppm): 1.20 (3H, s), 2.17-2.28 (1H, m), 2.37-2.44 (1H, m), 2.77-2.82 (1H, m), 3.38 (1H (—OH), d, J=2 Hz), 3.49 (1H, dd, J=9 Hz, J=4 Hz), 3.56 (1H, dd, J=9 Hz, J=6 Hz), 3.90-3.96 (1H, m), 4.22-4.28 (1H, m), 4.39-4.45 (1H, m).

Example 2 Synthesis of (1'R*,2S*)-2-(1',2'-dihydroxyethyl)-4-butanolide

Compound Having Relative Configuration Represented by the Formula (VIII)

(1'R*,2S*)-2-[2'-(1,1-Dimethylethoxy)-1'-hydroxyethyl]-4-butanolide (1.3 g) was added to trifluoroacetic acid (4 mL) and the mixture was stirred on an ice bath for 90 min. Trifluoroacetic acid was evaporated under reduced pressure to give the title compound (1.0 g).

$^1$H-NMR (CDCl$_3$, δppm): 2.10-2.20 (1H, m), 2.37-2.44 (1H, m), 2.80-2.87 (1H, m), 3.6-3.8 (1H (—OH), br), 3.67 (1H, dd, J=12 Hz, J=6 Hz), 3.75 (1H, dd, J=12 Hz, J=3 Hz), 3.86-3.90 (1H, m), 4.24-4.30 (1H, m), 4.43 (1H, dt, J=9 Hz, J=3 Hz), 4.4-4.5 (1H (—OH), br).

Example 3 Synthesis of (2S*,4'R*)-2-(2',2'-dimethyl-[1',3']dioxolane-4'-yl)-4-butanolide Compound Having Relative Configuration Represented by the Formula (IX)

2,2-Dimethoxypropane (15 mL) was added to (1'R*,2S*)-2-(1',2'-dihydroxyethyl)-4-butanolide (1.0 g), p-toluenesulfonic acid monohydrate (50 mg) was added, and the mixture was stirred at room temperature for 2 hr. The reaction mixture was poured into saturated aqueous sodium hydrogen carbonate solution (100 mL), extracted twice with MTBE (50 mL). The organic layer was thoroughly washed with saturated aqueous sodium hydrogen carbonate solution, and the solvent was evaporated to give the title compound (0.75 g).

$^1$H-NMR (CDCl$_3$, δppm): 1.36 (3H, s), 1.42 (3H, s), 2.18-2.28 (1H, m), 2.37-2.47 (1H, m), 2.88-2.95 (1H, m), 3.97 (1H, dd, J=9 Hz, J=6 Hz), 4.08 (1H, dd, J=9 Hz, J=7 Hz), 4.19-4.36 (1H, m), 4.37-4.45 (1H, m), 4.45-4.49 (1H, m).

Example 4 Synthesis of (3S*,4'R*)-3-(2',2'-dimethyl-[1',3']dioxolane-4'-yl)tetrahydrofuran-2-ol Compound Having Relative Configuration Represented by the Formula (XI)

(2S*,4'R*)-2-(2',2'-Dimethyl-[1',3']dioxolane-4'-yl)-4-butanolide (400 mg) was dissolved in dichloromethane (4 mL), and DIBAL-H 1.0 M toluene solution (2.4 mL) was added at around −78° C. The mixture was stirred at said temperature for 1 hr. The reaction mixture was poured into saturated aqueous ammonium chloride solution (2 mL) and extracted with MTBE (7.5 mL). The organic layer was dried over anhydrous magnesium sulfate, and a small amount of a filtering aid (celite, manufactured by Celite Corporation) was added. The mixture was filtrated and the solvent was evaporated to give the title compound (340 mg).

$^1$H-NMR (CDCl$_3$, δppm): 1.35 (3H, s), 1.44 (3H, s), 1.45-1.58 (1H, m), 1.78-1.85 (1H, m), 2.08-2.35 (2H, m), 3.62-3.72 (1H, m), 3.86-4.08 (3H, m), 4.10-4.17 (0.5H, s), 4.27-4.33 (0.5H, m).

Example 5 Synthesis of (3R*,3aS*,6aR*)-hexahydrofuro[2,3-b]furan-3-ol

Compound Having a Relative Configuration Represented by the Formula (XV)

(3S*,4'R*)-3-(2',2'-Dimethyl-[1',3']dioxolane-4'-yl)tetrahydrofuran-2-ol (120 mg) was dissolved in THF (2 mL), and 6N hydrochloric acid (0.1 mL) was added. The mixture was stirred at room temperature for 20 min. 10% Aqueous sodium hydrogen carbonate solution (2 mL) was added to the reaction mixture and the mixture was extracted with ethyl acetate (2 mL). After washing with 10% brine (2 mL), the extract was dried over anhydrous magnesium sulfate and the solvent was evaporated to give the title compound (50 mg). $^1$H-NMR did not show a peak of stereoisomer.

$^1$H-NMR (CDCl$_3$, δppm): 1.73 (1H (—OH), d, J=6 Hz), 1.82-1.93 (1H, m), 2.28-2.34 (1H, m), 2.82-2.89 (1H, m), 3.65 (1H, dd, J=9 Hz, J=7 Hz), 3.88-3.94 (1H, m), 3.97-4.02 (2H, m), 4.42-4.49 (1H, m), 5.70 (1H, d, J=5 Hz).

Example 6 Synthesis of (1'R*,2S*)-2-[2'-benzyloxy-1'-hydroxyethyl]-4-butanolide Compound Having a Relative Configuration Represented by the Formula (VII)

Ethyl 4-benzyloxyacetoacetate (42.1 g) synthesized according to the method describe in U.S. Pat. No. 5,399,722 was dissolved in methanol (300 mL) and sodium borohydride (3.03 g) was added at a temperature of from 5° C. to 10° C. The mixture was stirred for 1 hr and water (300 mL) was added. The solvent was mostly evaporated, and the organic layer extracted twice with MTBE (300 mL) was washed twice with 2% sodium hydrogen carbonate (100 mL) and washed twice with saturated brine (150 mL), dried over anhydrous magnesium sulfate and filtrated. MTBE was evaporated to give ethyl (±)-4-benzyloxy-3-hydroxybutanoate (38.8 g). To a solution of lithium diisopropylamide 1.5 M cyclohexane solution (190 mL) in THF (200 mL) was added a solution of ethyl (±)-4-benzyloxy-3-hydroxybutanoate (29.4 g) in THF (50 mL) at a temperature of from −78° C. to −60° C. and the temperature was raised to −20° C. Separately, 2-iodoethanol (34.4 g) and ethyl vinyl ether (23.1 g) were mixed in the presence of p-toluenesulfonic acid monohydrate (20 mg) to give 2-(1-ethoxyethoxy)ethyl iodide (47.9 g) and 39.3 g thereof was added dropwise at a temperature near −20° C. to 0° C. The mixture was stirred overnight at room temperature. The reaction mixture was poured into a 1N aqueous hydrochloric acid (450 mL), and the mixture was extracted twice with MTBE (200 mL) and washed with saturated aqueous sodium hydrogen carbonate solution. The solvent was evaporated and methanol (300 mL) and p-toluenesulfonic acid monohydrate (5.3 g) were added to the residue. The mixture was stirred at room temperature for 6 hr. Triethylamine (2.0 g) was added to the reaction mixture and the solvent was mostly evaporated. The residue was extracted with ethyl acetate (300 mL). The organic layer was washed with water (150 mL) and saturated aqueous sodium hydrogen carbonate solution (150 mL) and dried over anhydrous magnesium sulfate. The solvent was evaporated. Diisopropyl ether (120 mL) was added to the residue and the mixture was recrystallized to give the title compound (5.65 g) (yellow fine crystals). The peak of syn-form (1'R*,2R*-body) was not detected in NMR and HPLC under the following conditions.

$^1$H-NMR (CDCl$_3$, δppm): 2.06-2.17 (1H, m), 2.27-2.33 (1H, m), 2.78-2.85 (1H, m), 3.62 (1H (—OH), br), 3.61-3.67 (2H, m), 3.97-4.01 (1H, m), 4.18-4.24 (1H, m), 4.39 (1H, dt, J=9 Hz, J=3 Hz), 4.55 (1H, d, J=12 Hz), 4.63 (1H, d, J=12 Hz), 7.26-7.37 (5H, m).

HPLC conditions: Daicel Chiralcel OD-H (0.46 cmφ×25 cm, 9/1 hexane/2-propanol; 1 ml/min, 254 nm) syn-(1'R,2R) t$_r$=15 min; syn-(1'S,2S) t$_r$=17 min; anti-(1'R,2S) or anti-(1'S, 2R) t$_r$=19 min or t$_r$=24 min.

Example 7 Synthesis of (1'R*,2S*)-2-(1',2'-dihydroxyethyl)-4-butanolide

Compound Having Relative Configuration Represented by the Formula (VIII)

(1'R*,2S*)-2-(2'-Benzyloxy-1'-hydroxyethyl)-4-butanolide (2.00 g) was dissolved in ethyl acetate (30 mL) and 10% Pd/C (manufactured by N.E. Chemcat, 50% Wet PE-Type) (200 mg) was added. The mixture was stirred under atmospheric pressure of hydrogen at around 25° C. for 3 hr. The catalyst was filtered off and the solvent was evaporated to give the title compound (1.27 g). The spectrum data thereof were the same as those of Example 2.

Example 8 Synthesis of (1'R*,2S*)-2-[2'-benzyloxy-1'-(1''-ethoxyethoxy)ethyl]-4-butanolide Compound Having Relative Configuration Represented by the Formula (X)

(1'R*,2S*)-2-(2'-Benzyloxy-1'-hydroxyethyl)-4-butanolide (1.00 g) was dissolved in a mixed solvent of THF (10 mL) and MTBE (20 mL) and p-toluenesulfonic acid monohydrate (60 mg) was added. Then, ethyl vinyl ether (1.1 g) was added dropwise. The reaction mixture was stirred at room temperature for 3 hr. The mixture was poured into saturated aqueous sodium hydrogen carbonate solution, extracted with MTBE and washed well with saturated aqueous sodium hydrogen carbonate solution. The solvent was evaporated to give the title compound (1.24 g).

$^1$H-NMR (CDCl$_3$, δppm): 1.15 (1.5H, t, J=7 Hz), 1.19 (1.5H, t, J=7 Hz), 1.29 (1.5H, d, J=6 Hz), 1.31 (1.5H, d, J=6 Hz), 2.17-2.37 (2H, m), 2.92-2.98 (1H, m), 3.42-3.62 (2H, m), 3.70-3.78 (2H, m), 4.08-4.37 (3H, m), 4.54 (2H, s), 4.82 (1H, q, J=5 Hz), 7.26-7.36 (5H, m).

Example 9 Synthesis of (1'R*,3S*)-3-[2'-benzyloxy-1'-(1''-ethoxyethoxy)ethyl]tetrahydrofuran-2-ol Compound Having Relative Configuration Represented by the Formula (XII)

(1'R*,2S*)-2-[2'-Benzyloxy-1-(1''-ethoxyethoxy)ethyl]-4-butanolide (1.22 g) was dissolved in toluene (10 mL), and a solution (4.4 mL) of DIBAL-H (1.0 M) in toluene was added at around −78° C. The mixture was stirred at the same temperature for 1 hr. Saturated aqueous ammonium chloride solution (5 mL) was added to the reaction mixture, and after adding anhydrous magnesium sulfate, the mixture was filtered through a filtering aid (celite, manufactured by Celite Corporation). The solvent was evaporated to give the title compound (1.23 g).

$^1$H-NMR (CDCl$_3$, δppm): 1.11-1.24 (3H, m), 1.31 (3H, d, J=5 Hz), 1.62-1.83 (2H, m), 2.00-2.08 (0.5H, m), 2.20-2.38 (0.5H, m), 2.40-2.51 (0.5H, m), 2.63-2.80 (0.5H, m), 3.44-4.21 (7H, m), 4.48-4.61 (2H, m), 4.75-4.91 (1H, m), 5.39-5.53 (1H, m), 7.26-7.36 (5H, m).

Example 10 Synthesis of (3R*,3aS*,6aR*)-hexahydrofuro[2,3-b]furan-3-ol

Compound Having a Relative Configuration Represented by the Formula (XV)

(1'R*,3S*)-3-[2'-Benzyloxy-1'-(1''-ethoxyethoxy)ethyl] tetrahydrofuran-2-ol (1.22 g) was dissolved in ethyl acetate (20 mL), and 10% Pd/C (manufactured by N.E. Chemcat, 50% Wet PE-Type) (242 mg) was added. The mixture was stirred under atmospheric pressure of hydrogen at around 25° C. for 1 hr. The catalyst was filtered off, and the solvent was evaporated. THF (10 mL) and 6N hydrochloric acid (0.05 mL) were added and stirred at around 25° C. for 1 hr. Anhydrous potassium carbonate was added to the reaction mixture and the solvent was evaporated to give the title compound (0.49 g). The spectrum data of this compound were the same as those in Example 5.

Example 11 Synthesis of (2S*,4'R*)-2-(2',2'-dimethyl-[1',3']dioxolane-4'-yl)-4-butanolide Method for Directly Synthesizing Compound (IX) from Compound (VII)

(1'R*,2S*)-2-(2'-Benzyloxy-1'-hydroxyethyl)-4-butanolide (97 mg) was dissolved in acetone (2.5 mL), and 2,2-dimethoxypropane (0.5 mL), 10% Pd/C (manufactured by N.E. Chemcat, 50% Wet PE-Type) (48 mg) and ion-exchange resin (Amberlyst 15E(Dry), manufactured by Rohm & Haas) (1 mg) were added. The mixture was stirred under atmospheric pressure of hydrogen at around 25° C. for 2 hr. After filtering off the catalyst, the solvent was evaporated to give the title compound (70 mg). The spectrum data of this compound were the same as those in Example 3.

Example 12 Synthesis of (3S,3aR,6aS)-hexahydrofuro[2,3-b]furan-3-ol

In the same manner as in Example 6 and using ethyl (S)-4-benzyloxy-3-hydroxybutanoate that can be synthesized according to the method described in, for example, U.S. Pat. No. 5,399,722 instead of ethyl (±)-4-benzyloxy-3-hydroxybutanoate, (1'S,2R)-2-[2'-benzyloxy-1'-hydroxyethyl]-4-butanolide can be produced, by subsequently performing Example 7, (1'S,2R)-2-(1',2'-dihydroxyethyl)-4-butanolide can be produced, by subsequently performing Example 3, (2R,4'S)-2-(2',2'-dimethyl-[1',3']dioxolane-4'-yl)-4-butanolide can be produced, by subsequently performing Example 4, (3R,4'S)-3-(2',2'-dimethyl-[1',3']dioxolane-4'-yl)tetrahydrofuran-2-ol can be produced, and by subsequently performing Example 5, (3S,3aR,6aS)-hexahydrofuro[2,3-b]furan-3-ol can be produced.

Example 13 Synthesis of (3R,3aS,6aR)-hexahydrofuro[2,3-b]furan-3-ol

In the same manner as in Example 1 and using ethyl (R)-4-t-butoxy-3-hydroxybutanoate that can be synthesized according to the method described in, for example, Heterocycles 26, 2841 (1987) instead of ethyl (±)-4-t-butoxy-3-hydroxybutanoate, (1'R,2S)-2-[2'-(1,1-dimethylethoxy)-1'-hydroxyethyl]-4-butanolide can be produced, by subsequently performing Example 2, (1'R,2S)-2-(1',2'-dihydroxyethyl)-4-butanolide can be produced, by subsequently performing Example 3, (2S,4'R)-2-(2',2'-dimethyl-[1',3']dioxolane-4'-yl)-4-butanolide can be produced, by subsequently performing Example 4, (3S,4'R)-3-(2',2'-dimethyl-[1',3']dioxolane-4'-yl)tetrahydrofuran-2-ol can be produced, and by subsequently performing Example 5, (3R,3aS,6aR)-hexahydrofuro[2,3-b]furan-3-ol can be produced.

Reference Example 1 Synthesis of 2-benzyloxyethyl iodide

2-Benzyloxyethanol (85.0 g) and triethylamine (73.5 g) were dissolved in THF (500 mL) and methanesulfonyl chloride (76.8 g) was added dropwise at from 0° C. to 10° C. The mixture was stirred for 3 hr. 10% Aqueous sodium bicarbonate (300 mL) was poured into the reaction mixture, the mixture was partitioned and combined with an extract of the aqueous layer with MTBE (300 mL), and the mixture was washed with 10% aqueous sodium bicarbonate and saturated brine and dried over anhydrous magnesium sulfate. The solvent was evaporated to give 2-benzyloxyethyl methanesulfonate (124.0 g). The 2-benzyloxyethyl methanesulfonate (124.0 g) was dissolved in acetone (500 mL), and sodium iodide (130.0 g) was added. The mixture was stirred at from 50° C. to 60° C. for 3 hr. The reaction mixture was filtered and the solvent was evaporated. Water (300 mL) was added, and the mixture was extracted twice with toluene (300 mL). The toluene layer was washed successively with aqueous sodium hydrogen sulfite solution, water and brine and dried over anhydrous magnesium sulfate. The solvent was evaporated to give the title compound (127.0 g).

Example 14 Synthesis of ethyl (2S,3R)-4-benzyloxy-3-hydroxy-2-(2'-benzyloxyethyl)butanoate Compound Represented by the Formula (XVII)

Under a nitrogen stream, THF (140 mL) was added to diisopropylamine (20.9 g) and thereto was added a solution (120 mL) of 15 wt % n-butyllithium in hexane at from −60° C. to −65° C. Furthermore, ethyl (R)-4-benzyloxy-3-hydroxybutanoate (20.0 g) (99% ee or above) that can be synthesized according to the method described in U.S. Pat. No. 5,399,722 was added dropwise at from −55° C. to −65° C. The reaction mixture was warmed to −25° C. and 1,3-dimethyl-3,4,5,6-tetrahydro-2(1H)-pyrimidinone (60 g) was added. Then, 2-benzyloxyethyl iodide (27 g) synthesized according to Reference Example 1 was added dropwise at around −15° C. The reaction mixture was stirred at from −15° C. to −10° C. for 23 hr and 2 mol/L aqueous hydrochloric acid (160 mL) was added. The mixture was extracted twice with toluene (300 mL) and washed with 10% aqueous sodium bicarbonate. The solvent was evaporated to give a mixture (35.9 g) containing the title compound and a diastereomer thereof, ethyl (2R,3R)-4-benzyloxy-3-hydroxy-2-(2'-benzyloxyethyl)butanoate, at a ratio of 3:1. A part was isolated by preparative HPLC to give a pure title compound.

NMR spectrum of ethyl (2S,3R)-4-benzyloxy-3-hydroxy-2-(2'-benzyloxyethyl)butanoate $^1$H-NMR (CDCl$_3$, δppm): 1.19 (3H, t, J=7 Hz), 1.84-1.92 (1H, m), 2.00-2.10 (1H, m), 2.78-2.83 (1H, m), 3.43-3.57 (4H, m), 3.89-3.95 (1H, m), 4.08 (2H, q, J=7 Hz), 4.47 (2H, s), 4.53 (2H, s), 7.24-7.36 (10H, m).

Example 15 Synthesis of (2S,3R)-4-benzyloxy-3-hydroxy-2-(2'-benzyloxyethyl)butanoic acid Compound Represented by the Formula (XVIII) or a Salt Thereof The mixture (27.0 g) containing ethyl (2S,3R)-4-benzyloxy-3-hydroxy-2-(2'-benzyloxyethyl)butanoate and a diastereomer thereof, ethyl (2R,3R)-4-benzyloxy-3-hydroxy-2-(2'-benzyloxyethyl)butanoate, at a ratio of 3:1 was dissolved in methanol (200 mL), and 10% aqueous potassium hydroxide solution (57.8 g) was added. The mixture was heated at 60° C. for 2 hr. Water (600 mL) was added to the reaction mixture and the mixture was washed with toluene (200 mL), adjusted to pH 1 with 2 mol/L aqueous hydrochloric acid and extracted 3 times with toluene (300 mL). The toluene layer was washed with saturated brine (300 mL), concentrated and to the residue was added ethanol (100 mL). The solution was heated to 65° C. and dibenzylamine (27.0 g) was added. The salt obtained by cooling was recrystallized from ethanol (273 mL) and further recrystallized from ethanol (77 mL) to give a dibenzylamine salt (17.7 g) of the title compound (99% de or above).

NMR spectrum of dibenzylamine salt
$^1$H-NMR (CDCl$_3$, δppm): 1.89-2.07 (2H, m), 2.67-2.72 (1H, m), 3.48-3.60 (4H, m), 3.78 (4H, s), 3.87-3.91 (1H, m), 4.46 (2H, s), 6.4-6.7 (3H, br), 7.22-7.36 (20H, m).

This compound (17.5 g) was adjusted to not higher than pH 1 with 2 mol/L hydrochloric acid (100 mL), and the aqueous layer was extracted with toluene (150 mL), and further 3 times with 100 mL, washed with saturated brine and concentrated to give the title compound (9.4 g).
$^1$H-NMR (CDCl$_3$, δppm): 1.86-1.97 (1H, m), 1.99-2.08 (1H, m), 2.81-2.86 (1H, m), 3.50-3.61 (4H, m), 3.97-4.01 (1H, m), 4.49 (2H, s), 4.53 (2H, s), 7.24-7.35 (10H, m)
specific optical rotation $[\alpha]_D^{26}$ −3.5° (C=4.0, MeOH)

Example 16 Synthesis of (2S,4'R)-2-(2',2'-dimethyl-[1',3']dioxolane-4'-yl)-4-butanolide Compound Represented by the formula (IX)

(2S,3R)-4-Benzyloxy-3-hydroxy-2-(2'-benzyloxyethyl)butanoic acid (8.36 g) was dissolved in 2,2-dimethoxypropane (80 mL), and reacted with anhydrous magnesium sulfate (1.4 g), Amberlyst 15 (Dry) (1.3 g) and 10% palladium-carbon (1.7 g) under atmospheric pressure of hydrogen for 3 hr. The reaction mixture was filtered and the solvent was evaporated. 10% Aqueous sodium bicarbonate (200 mL) was added and the mixture was washed with heptane (100 mL) and extracted 3 times with ethyl acetate (200 mL). The organic layer was dried over anhydrous magnesium sulfate and the solvent was evaporated to give the title compound (3.0 g).

The spectrum data of this compound were the same as those in Example 3.
specific optical rotation $[\alpha]_D^{28}$ +16.4° (C=4.0, MeOH)

Example 17 Synthesis of (3S,4'R)-3-(2',2'-dimethyl-[1',3']dioxolane-4'-yl)tetrahydrofuran-2-ol Compound Represented by the Formula (XI)

(2S,4'R)-2-(2',2'-Dimethyl-[1',3']dioxolane-4'-yl)-4-butanolide (2.7 g) was dissolved in toluene (30 mL) and cooled to −78° C. 1.0 M DIBAL-H toluene solution (16 mL) was added, and the mixture was stirred at the same temperature for 2 hr. Saturated aqueous ammonium chloride solution (25 mL) and MTBE (20 mL) were added to the reaction mixture, anhydrous magnesium sulfate (10 g) and celite (5 g) were added, and the mixture was filtered. The residue was thoroughly extracted with ethyl acetate and combined with the filtrate. The solvent was evaporated to give the title compound (2.4 g).

The NMR spectrum of this compound was the same as that in Example 4.

Example 18 Synthesis of (3R,3aS,6aR)-hexahydrofuro[2,3-b]furan-3-ol

Compound Represented by the Formula (XV)

(3S,4'R)-3-(2',2'-Dimethyl-[1',3']dioxolane-4'-yl)tetrahydrofuran-2-ol (2.4 g) was dissolved in THF (20 mL), and 2 mol/L hydrochloric acid (3.2 mL) was added. The mixture was stirred at room temperature for 16 hr. Water (30 mL) and sodium hydrogen carbonate (5 g) were added to the reaction mixture, and the mixture was washed twice with heptane (15 mL). Sodium chloride was added to the aqueous layer to saturation and the mixture was extracted 10 times with ethyl acetate (50 mL). Ethyl acetate was concentrated to give an almost pure title compound (1.4 g).

The NMR spectrum data of this compound were the same as those in Example 5.
specific optical rotation $[\alpha]_D^{26}$ −12.0° (C=5.6, MeOH)

Example 19 Synthesis of ethyl (2S,3R)-4-benzyloxy-3-hydroxy-2-[2'-(1,1-dimethylethoxy)ethyl]butanoate Compound Represented by the Formula (XVII)

Under a nitrogen stream, THF (200 mL) was added to diisopropylamine (23.4 g). To the resulting solution was added a solution (140 mL) of 15 wt % n-butyllithium in hexane at from −60° C. to −65° C. Further, ethyl (R)-4-benzyloxy-3-hydroxybutanoate (25.0 g) (99% ee or above) that can be synthesized by the method described in U.S. Pat. No. 5,399,722 was added dropwise at from −55° C. to −65° C. The reaction mixture was warmed to −25° C. and 2-t-butoxyethyl iodide (26.4 g) synthesized according to Reference Example 1 using 2-t-butoxyethanol as a material instead of 2-benzyloxyethanol was added dropwise at around −20° C. The reaction mixture was stirred at room temperature for 24 hr, 2 mol/L aqueous hydrochloric acid (200 mL) was added, and the mixture was extracted twice with MTBE (250 mL) and washed with 10% aqueous sodium bicarbonate. The solvent was evaporated to give a mixture (35.9 g) containing the title compound and a diastereomer thereof, ethyl (2R,3R)-4-benzyloxy-3-hydroxy-2-[2'-(1,1-dimethylethoxy)ethyl]butanoate, at a ratio of about 3:1. A part thereof was isolated by preparative HPLC to give a pure title compound.

NMR spectrum of ethyl (2S,3R)-4-benzyloxy-3-hydroxy-2-[2'-(1,1-dimethylethoxy)ethyl]butanoate
$^1$H-NMR (CDCl$_3$, δppm): 1.15 (3H, s), 1.23 (3H, t, J=7 Hz), 1.74-1.82 (1H, m), 1.93-2.02 (1H, m), 2.76-2.81 (1H, m), 3.30-3.62 (4H, m), 3.90-3.98 (1H, m), 4.11 (2H, q, J=7 Hz), 4.54 (2H, s), 7.24-7.35 (5H, m).

Example 20 Synthesis of (2S,3R)-4-benzyloxy-3-hydroxy-2-[2'-(1,1-dimethylethoxy)ethyl]butanoic acid Compound Represented by the Formula (XVIII) or a Salt Thereof A mixture (10.3 g) containing ethyl (2S,3R)-4-benzyloxy-3-hydroxy-2-[2'-(1,1-dimethylethoxy)ethyl]butanoate and a diastereomer thereof, ethyl (2R,3R)-4-benzyloxy-3-hydroxy-2-[2'-(1,1-dimethylethoxy)ethyl]butanoate, at a ratio of about 3:1 was dissolved in methanol (30 mL), and 20% aqueous potassium hydroxide solution (13 g) was added. The mixture was heated at 60° C. for 2 hr. Methanol was evaporated and water (200 mL) was added and the mixture was washed twice with toluene (100 mL), and adjusted to pH 1 with 2 mol/L aqueous hydrochloric acid. The mixture was extracted twice with toluene (100 mL). The toluene layer was washed with saturated brine (100 mL), concentrated and to the concentrated residue was added methanol (18 mL). The solution was heated to 65° C., dibenzylamine (4.2 g) was added and the mixture was cooled to give a salt, which was recrystallized from ethanol (25 mL) and further recrystallized from ethanol (77 mL), (60 mL) to give a dibenzylamine salt (2.03 g) of the title compound (99% de or above). This compound (2.0 g) was adjusted to not higher than pH 1 with 2 mol/L hydrochloric acid (10 mL) and the aqueous layer was extracted with toluene (20 mL), (50 mL), washed with saturated brine and concentrated to give the title compound (1.2 g).

Example 21 Synthesis of (1'R,2S)-2-[2'-benzyloxy-1'-hydroxyethyl]-4-butanolide

Compound Represented by the Formula (VII)

(2S,3R)-4-Benzyloxy-3-hydroxy-2-[2'-(1,1-dimethylethoxy)ethyl]butanoic acid (0.80 g) was dissolved in THF (10 mL) and trifluoromethanesulfonic acid (122 mg) was added. The mixture was stirred at room temperature for 3 days. The solvent was evaporated from the reaction mixture, the residue was washed with heptane (100 mL) and extracted with 10% aqueous sodium bicarbonate (100 mL), (200 mL) into the aqueous layer. The aqueous layer was extracted 3 times with ethyl acetate (100 mL), washed with saturated brine, and dried over anhydrous magnesium sulfate. The solvent was evaporated to give the title compound (0.37 g) as pale yellow crystals.

The NMR spectrum of this compound was the same as that in Example 6.

Only a peak corresponding to anti-(1'R,2S)-form was found under the HPLC conditions using the optically active column of Example 6, and the peaks of other isomers were below detection level.

Example 22 Synthesis of (1'R,2R)-2-[2'-benzyloxy-1'-hydroxyethyl]-4-butanolide

Compound (XXII)

2-Benzyloxyacetyl-γ-butyrolactone (29.7 g) that can be synthesized according to the method described in JP-A-10-218881 was dissolved in ethanol (300 mL) and a solution of benzene ruthenium(II) chloride dimer (318 mg) and (S)-(−)-BINAP (791 mg) in DMF (30 mL) was reacted under a hydrogen atmosphere at 500 kPa, 100° C. for 3 hr. The reaction mixture was poured into 5% aqueous sodium hydrogen carbonate solution, extracted with ethyl acetate, and washed with brine. The catalyst was removed by flash chromatography to give an isomer mixture (23.5 g) mainly containing the title compound. The syn:anti diastereomer ratio of the obtained compound was 11:2, and the optical purity of the syn-form (1'R,2R-form) was 78% ee. Syn-form: $^1$H-NMR (CDCl$_3$, δppm): 2.14-2.22 (1H, m), 2.33-2.43 (1H, m), 2.73 (1H, dt, J=10 Hz, J=4 Hz), 2.79 (1H (—OH), d, J=5 Hz), 3.55 (2H, d, J=6 Hz), 4.16-4.23 (1H, m), 4.28-4.33 (1H, m), 4.36 (1H, dt, J=9 Hz, J=3 Hz), 4.54 (1H, d, J=12 Hz), 4.57 (1H, d, J=12 Hz), 7.26-7.38 (5H, m).

HPLC condition: Daicel Chiralcel OD-H (0.46 cmφ×25 cm, 9/1 hexane/2-propanol; 0.8 ml/min, 254 nm) syn-(1'R, 2R) t$_r$=16 min; syn-(1'S,2S) t$_r$=19 min; anti-(1'R,2S) or anti-(1'S,2R) t$_r$=21 min or t$_r$=26 min.

Example 23 Synthesis of (2R,4'R)-2-(2',2'-dimethyl-[1',3']dioxolane-4'-yl)-4-butanolide Compound (XXIV)

(1'R,2R)-2-(2'-Benzyloxy-1'-hydroxyethyl)-4-butanolide (23.5 g) obtained in Example 22 was dissolved in acetone (150 mL), and 2,2-dimethoxypropane (40 mL), 10% Pd/C (manufactured by N.E. Chemcat, 50% Wet PE-Type) (3.0 g) and Amberlyst 15E(Dry) (0.94 g) were added. The mixture was stirred under an atmospheric pressure of hydrogen for 22 hr. After filtering off the catalyst, the solvent was evaporated to give the title compound (17.7 g).
$^1$H-NMR (CDCl$_3$, δppm): 1.36 (3H, s), 1.42 (3H, s), 2.28-2.44 (2H, m), 2.68-2.74 (1H, m), 3.85 (1H, dd, J=9 Hz, J=6 Hz), 4.22 (1H, dd, J=9 Hz, J=6 Hz), 4.26-4.30 (1H, m), 4.35-4.44 (2H, m).

Example 24 Synthesis of (3R,4'R)-3-(2',2'-dimethyl-[1',3']dioxolane-4'-yl)tetrahydrofuran-2-ol Compound (XXV)

(2R,4'R)-2-(2',2'-dimethyl-[1',3']dioxolane-4'-yl)-4-butanolide (17.7 g) obtained in Example 23 was dissolved in THF (150 mL) and a solution (100 mL) of DIBAL-H 1.0 M in toluene was added at around −70° C. The mixture was stirred at the same temperature for 3.5 hr. The reaction mixture was poured into saturated aqueous ammonium chloride solution (120 mL) and extracted with MTBE (100 mL). The organic layer was dried over anhydrous magnesium sulfate, and after adding a small amount of filtering aid (celite), filtered. The solvent was evaporated to give the title compound (13.8 g).
$^1$H-NMR (CDCl$_3$, δppm): 1.36, 1.37 (total 3H, each s), 1.43, 1.44 (total 3H, each s), 1.82-1.93, 2.03-2.43 (total 3H, each m), 3.15-3.43 (1H, —OH, br), (1H, m), 3.62-3.71 (1H, m), 3.84-4.43 (4H, m), 5.24-5.26, 5.33-5.36 (total 1H, each m).

Example 25 Synthesis of (3R,3aR,6aS)-hexahydrofuro[2,3-b]furan-3-ol

Compound (XXVI)

(3R,4'R)-3-(2',2'-Dimethyl-[1',3']dioxolane-4'-yl)tetrahydrofuran-2-ol (13.8 g) obtained in Example 24 was dissolved in THF (120 mL), and 6N hydrochloric acid (4 mL) was added. The mixture was stirred overnight at room temperature. Anhydrous potassium carbonate (25 g) was added to the reaction mixture and the mixture was filtered. The concentrated residue was dissolved in toluene (20 mL) with heating and diisopropyl ether (30 mL) was added. The mixture was stirred at room temperature and the resulting crystals were collected by filtration and dried to give the title compound (2.8 g, 88% ee), which was almost a pure syn-form.
$^1$H-NMR (CDCl$_3$, δppm): 1.67-1.75 (1H, m), 1.95-2.05 (1H (—OH), br), 2.13-2.23 (1H, m), 2.79-2.84 (1H, m), 3.81-3.91 (3H, m), 3.98 (1H, dd, J=10 Hz, J=3 Hz), 4.23 (1H, d, J=3 Hz), 5.89 (1H, d, J=5 Hz).

Example 26 Synthesis of (3S,3aR,6aS)-hexahydrofuro[2,3-b]furan-3-yl benzoate

Compound (XXVIII)

(3R,3aR,6aS)-Hexahydrofuro[2,3-b]furan-3-ol (125 mg) obtained in Example 25 was dissolved in toluene (2 mL). Benzoic acid (214 mg), a 40 wt % solution (705 mg) of diethyl azodicarboxylate in toluene, and triphenylphosphine (416 mg) were added. The mixture was stirred overnight. After the reaction, 10% of the solution was purified by flash chromatography to give the title compound (12 mg) (88% ee), which was almost a pure anti-form.
$^1$H-NMR (CDCl$_3$, δppm): 1.94-2.01 (1H, m), 2.10-2.15 (1H, m), 3.17-3.23 (1H, m), 3.94 (1H, dd, J=10 Hz, J=6 Hz), 3.99-4.05 (2H, m), 4.20 (1H, dd, J=10 Hz, J=6 Hz), 5.45-5.51

(1H, m), 5.80 (1H, d, J=5 Hz), 7.47 (2H, t, J=8 Hz), 7.58 (1H, t, J=8 Hz), 8.04 (1H, d, J=8 Hz)

Example 27 Synthesis of (3S,3aR,6aS)-hexahydrofuro[2,3-b]furan-3-ol

Compound (XV)

Toluene (20 mL) was added to 90% of the solution after reaction, which was obtained in Example 26, and the mixture was washed 3 times with water (20 mL). The solvent was evaporated and methanol (20 mL) was added to the residue. 10% Aqueous sodium hydroxide solution (20 mL) was poured thereinto and the mixture was stirred for 30 min. The solvent was evaporated and water (30 mL) was poured into the residue. The mixture was washed twice with toluene (20 mL) and sodium chloride was added to the aqueous layer to saturation. The mixture was extracted 3 times with ethyl acetate (20 mL) and dried over anhydrous magnesium sulfate. The solvent was evaporated to give the title compound (98 mg, 88% ee) as an oil, which was an almost pure anti-form.
$^1$H-NMR (CDCl$_3$, δppm): 1.73 (1H (—OH), d, J=6 Hz), 1.82-1.93 (1H, m), 2.28-2.34 (1H, m), 2.82-2.89 (1H, m), 3.65 (1H, dd, J=9 Hz, J=7 Hz), 3.88-3.94 (1H, m), 3.97-4.02 (2H, m), 4.42-4.49 (1H, m), 5.70 (1H, d, J=5 Hz).

The optical purity was measured by HPLC under the following conditions after benzoylation by a conventional method.

HPLC condition: Daicel Chiralcel OD-H (0.46 cmφ×25 cm, 19/1 hexane/2-propanol; 1 ml/min, 254 nm) (3S,3aR,6aS)-form t$_r$=13 min, (3R,3aS,6aR)-form t$_r$=14 min Example 28 Synthesis of (3aR,6aS)-hexahydrofuro[2,3-b]furan-3-on Compound (XXVII)

A solution of oxalyl chloride (510 mg) in methylene chloride (10 mL) was cooled to −78° C. and a solution of dimethyl sulfoxide (421 mg) in methylene chloride (2 mL) was added dropwise. The mixture was stirred for 10 min and a solution of (3R,3aR,6aS)-hexahydrofuro[2,3-b]furan-3-ol (260 mg, 88% ee) obtained in Example 25 in methylene chloride (5 mL) was added dropwise at the same temperature. The mixture was stirred for 15 min and the reaction mixture was warmed to −45° C. over 1 hr. Triethylamine (2.4 mL) was poured thereinto and the mixture was warmed to 0° C. Saturated aqueous ammonium chloride solution (8 mL) was added to the reaction mixture and the mixture was extracted twice with ethyl acetate (20 mL). The organic layer was washed with saturated aqueous ammonium chloride solution and the solvent was evaporated. The residue was purified by flash chromatography to give the title compound (82 mg, 88% ee) as crystals.
$^1$H-NMR (CDCl$_3$, δppm): 2.20-2.26 (2H, m), 2.97-3.01 (1H, m), 3.77-3.83 (1H, m), 4.03-4.07 (1H, m), 4.15 (2H, s), 6.07 (1H, d, J=5 Hz).

Example 29 Synthesis of (3S,3aR,6aS)-hexahydrofuro[2,3-b]furan-3-ol

Compound (XV)

To a suspension of lithium aluminum hydride (15 mg) dispersed in THF (0.2 mL) was added dropwise a solution of (3aR,6aS)-hexahydrofuro[2,3-b]furan-3-on (64 mg) obtained in Example 28 in THF (0.5 mL) at 0° C. and the mixture was stirred for 1 hr. Water (0.1 mL), 15 aqueous sodium hydroxide solution (0.1 mL) and water (0.3 mL) were successively added to the reaction mixture every 30 min and the mixture was filtered and washed well with THF. The filtrate was dried over anhydrous magnesium sulfate, filtered and the solvent was evaporated to give the title compound (57 mg, 88% ee) as an oil, which was an almost pure anti-form. The spectrum data were the same as those in Example 27.

Example 30 Synthesis of (1'S,2S)-2-[2'-benzyloxy-1'-hydroxyethyl]-4-butanolide

Compound (XXII)

In the same manner as in Example 22 except that 2-benzyloxyacetyl-γ-butyrolactone (14.2 g) was used and (R)-(+)-BINAP was used instead of (S)-(−)-BINAP, the title compound (10.8 g) was obtained as an oil. The syn:anti diastereomer ratio of the obtained product was 12:1, and the optical purity of the syn-form (1'S,2S-form) was 82% ee. The spectrum data were the same as those in Example 22.

Example 31 Synthesis of (2S,4'S)-2-(2',2'-dimethyl-[1',3']dioxolane-4'-yl)-4-butanolide Compound (XXIV)

In the same manner as in Example 23 except that (1'S,2S)-2-[2'-benzyloxy-1'-hydroxyethyl]-4-butanolide (10.7 g) obtained in Example 30 was used instead of (1'R,2R)-2-(2'-benzyloxy-1'-hydroxyethyl)-4-butanolide, the title compound (6.8 g) was obtained as an oil. The spectrum data were the same as those in Example 23.

Example 32 Synthesis of (3S,4'S)-3-(2',2'-dimethyl-[1',3']dioxolane-4'-yl)tetrahydrofuran-2-ol Compound (XXV)

In the same manner as in Example 24 except that (2S,4'S)-2-(2',2'-dimethyl-[1',3']dioxolane-4'-yl)-4-butanolide (5.4 g) obtained in Example 31 was used instead of (2R,4'R)-2-(2',2'-dimethyl-[1',3']dioxolane-4'-yl)-4-butanolide, the title compound (4.7 g) was obtained as an oil. The spectrum data were the same as those in Example 24.

Example 33 Synthesis of (3S,3aS,6aR)-hexahydrofuro[2,3-b]furan-3-ol

Compound (XXVI)

In the same manner as in Example 25 except that (3S,4'S)-3-(2',2'-dimethyl-[1',3']dioxolane-4'-yl)tetrahydrofuran-2-ol (3.2 g) obtained in Example 32 was used instead of (3R,4'R)-3-(2',2'-dimethyl-[1',3']dioxolane-4'-yl)tetrahydrofuran-2-ol, the title compound (1.5 g) was obtained as pale yellow crystals. The spectrum data were the same as those in Example 25.

Example 34 Synthesis of (3R,3aS,6aR)-hexahydrofuro[2,3-b]furan-3-yl benzoate

Compound (XXVIII)

In the same manner as in Example 26 except that (3S,3aS,6aR)-hexahydrofuro[2,3-b]furan-3-ol (1.0 g) obtained in Example 33 was used instead of (3R,3aR,6aS)-hexahydrofuro[2,3-b]furan-3-ol and by separating and purifying a part, the title compound was obtained as an oil. The spectrum data were the same as those in Example 26. The optical purity was 89% ee.

Example 35 Synthesis of (3R,3aS,6aR)-hexahydrofuro[2,3-b]furan-3-ol

Compound (XV)

In the same manner as in Examples 26, 27 except that (3S,3aS,6aR)-hexahydrofuro[2,3-b]furan-3-ol (1.0 g) obtained in Example 33 was used instead of (3R,3aR,6aS)-hexahydrofuro[2,3-b]furan-3-ol, the title compound (0.72 g, 89% ee) was obtained as an oil. The spectrum data were the same as those in Example 27.

Example 36 Synthesis of (1'S,2S)-2-(2'-benzyloxy-1'-hydroxyethyl)-4-butanolide 2-Benzyloxyacetyl-γ-butyrolactone (30.0 g) was dissolved in ethanol (227 mL) and a solution (64 mL) of dichloro(1,5-cyclooctadiene)ruthenium (II) polymer (240 mg) and (R)-(+)-BINAP (615 mg) in tetrahydrofuran was added. The mixture was reacted under a hydrogen atmosphere at 600 kPa and 70° C. for 3 hr. The mixture was allowed to cool to room temperature and water (300 mL) and methanol (220 mL) were added. The mixture was washed 4 times with heptane (200 mL) to remove insoluble materials. The water-methanol solution was applied to a rotary evaporator to remove methanol and ethanol. Salt was added to saturate the aqueous solution and the mixture was extracted with ethyl acetate (300 mL). The extract was dried over anhydrous magnesium sulfate, colored substances were removed with activated carbon and ethyl acetate was removed by a rotary evaporator. By this method, an isomeric compound (19.7 g) mainly containing the title compound was obtained. The syn:anti diastereomer ratio of the obtained compound was 7:1, and the optical purity of the syn form (1'S,2S form) was 74% ee.

Example 37 Synthesis of (2S,2'S)-2-(1',4'-dioxa-spiro[4.5]-2'-decyl)-4-butanolide (1'S,2S)-2-(2'-Benzyloxy-1'-hydroxyethyl)-4-butanolide (19.6 g) was dissolved in acetone (80 mL), and 1,1-dimethoxycyclohexane (45 mL), 5% palladium on carbon (wet PH-Type, Kawaken Fine Chemicals Co., Ltd.) (3.92 g) and Amberlist 15E (Dry) (0.98 g) were sequentially added. The mixture was reacted under a hydrogen atmosphere at 600 kPa and room temperature for 3 hr. Celite and anhydrous magnesium sulfate were added to the mixture and, after stirring the mixture at room temperature for 30 min, celite and anhydrous magnesium sulfate were filtered off. The filtrate was applied to a rotary evaporator to remove acetone to dry. By this method, the title compound (17.1 g) was obtained.

$^1$H-NMR (CDCl$_3$, δppm): 1.35-1.44 (4H, m), 1.55-1.89 (6H, m), 2.32-2.42 (2H, m), 2.69 (1H, dt, J=9.6 Hz, J=5.6 Hz), 3.84 (1H, dd, J=8.8 Hz, J=6.4 Hz), 4.18-4.30 (2H, m), 4.35-4.50 (2H, m).

Example 38 Synthesis of (3S,2'S)-3-(1',4'-dioxa-spiro[4.5]-2'-decyl)tetrahydrofuran-2-ol (2S,2'S)-2-(1',4'-Dioxa-spiro[4.5]-2'-decyl)-4-butanolide (10.1 g) was dissolved in toluene (67 mL) and the solution was cooled to −78° C. A 1M solution (71.4 mL) of diisobutylaluminum hydride in toluene was added dropwise while maintaining the reaction temperature at not higher than −70° C. The mixture was stirred at −78° C. for 1 hr and slowly added to an aqueous solution (500 mL) of potassium sodium tartarate tetrahydrate (225 g). Acetic acid (20 mL) was added and the mixture was stirred overnight at room temperature, and extracted with ethyl acetate. The extract was washed with saturated aqueous sodium hydrogen carbonate solution (300 mL) and saturated brine (300 mL), and dried over anhydrous magnesium sulfate. Colored substances were removed with activated carbon and ethyl acetate was removed by a rotary evaporator to dry. By this method, the title compound (7.06 g) was obtained.

$^1$H-NMR (CDCl$_3$, δppm): 1.36-1.44 (4H, m), 1.55-1.93 (6H, m), 2.05-2.34 (2H, m), 2.51 (0.75H, brs), 3.07 (0.25H, d, J=5 Hz), 3.60-4.33 (5H, m), 5.25 (0.75H, s), 5.35 (0.25H, t, J=5 Hz).

Example 39 Synthesis of (3S,3aS,6aR)-hexahydrofuro[2,3-b]furan-3-ol (3S,2'S)-3-(1',4'-Dioxa-spiro[4.5]-2'-decyl)tetrahydrofuran-2-ol (9.3 g) was dissolved in tetrahydrofuran (49 mL) and 6N aqueous hydrochloric acid solution (3.5 ml) was added dropwise at room temperature. The mixture was stirred overnight at room temperature and anhydrous potassium carbonate (9.0 g) was added. Anhydrous potassium carbonate was filtered off and the filtrate was applied to a rotary evaporator to remove tetrahydrofuran to dry. The crude reaction product was distilled under reduced pressure with an oil vacuum pump and the obtained colorless liquid was recrystallized from a mixed solvent of ethyl acetate and heptane to give the title compound (2.19 g).

INDUSTRIAL APPLICABILITY

According to the present invention, a production method of a compound represented by the formula (XIV), particularly the formula (XV), useful as an intermediate for an anti-AIDS drug, free of using ozone oxidation or highly toxic reagent, as well as an intermediate to be used for the method and a production method thereof can be provided. In addition, a method for efficiently producing a compound having an absolute configuration represented by the formula (XV) and an enantiomer thereof without using a technique such as optical resolution and the like or a highly toxic reagent, as well as an intermediate to be used for the method and a production method thereof can be provided. Furthermore, according to the present invention, a compound represented by the formula (XIV), particularly the formula (XV), can be provided economically on an industrial scale.

This application is based on a patent application Nos. 382584/2002 and 171303/2003 filed in Japan, the contents of which are hereby incorporated by reference.

The invention claimed is:

1. A method for producing a compound having a configuration represented by the formula (XXVI):

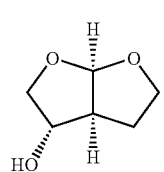

(XXVI)

or the enantiomer thereof
wherein the method comprises
deprotecting and cyclizing a compound having a configuration represented by the formula (XXV):

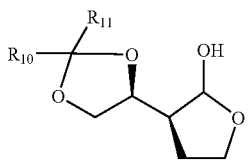

(XXV)

or the enantiomer thereof
wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an α,ω-alkylene group having 2 to 5 carbon atoms, wherein one of the carbon atoms at positions other than α-position and ω-position is optionally substituted by an oxygen atom or a sulfur atom,
with an acid to form a compound having a configuration represented by the formula (XXVI) or the enantiomer thereof, wherein the acid is selected from a group consisting of hydrochloric acid, sulfuric acid, phosphoric acid, methanesulfonic acid, p-toluenesulfonic acid, and a strong acidic ion-exchange resin.

2. The method of claim 1, wherein $R_{10}$ and $R_{11}$ are the same or different and each is independently a hydrogen atom, a lower alkyl group, a lower alkoxyl group or a phenyl group.

3. A method for producing a compound having a configuration represented by the formula (XXVI):

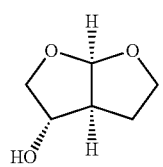

(XXVI)

or the enantiomer thereof
wherein the method comprises
(1) stereoselectively reducing a compound represented by the formula (XXI):

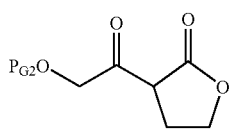

(XXI)

wherein $P_{G2}$ is a hydroxy-protecting group,
to form a compound having a configuration represented by the formula (XXII):

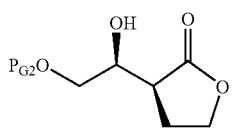

(XXII)

or the enantiomer thereof
wherein $P_{G2}$ is as defined above, (2) using the compound having a configuration represented by the formula (XXII) or the enantiomer thereof in a reaction to form a compound having a configuration represented by the formula (XXIV):

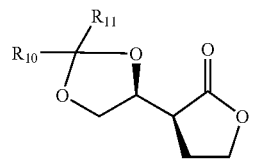

(XXIV)

or the enantiomer thereof
wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an α,ω-alkylene group having 2 to 5 carbon atoms, wherein one of the carbon atoms at positions other than α-position and ω-position is optionally substituted by an oxygen atom or a sulfur atom, wherein the reaction comprises the following step (A) or (B):

(A) simultaneously deprotecting the compound having a configuration represented by the formula (XXII) or the enantiomer thereof and introducing a diol protecting group into the compound having a configuration represented by the formula (XXII) or the enantiomer thereof
or (B) deprotecting the compound having a configuration represented by the formula
(XXII) or the enantiomer thereof to form a compound having a configuration represented by the formula (XXIII):

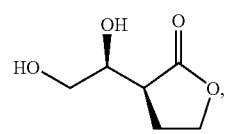

(XXIII)

or the enantiomer thereof, and
introducing a diol protecting group into the compound having a configuration represented by the formula (XXIII) or the enantiomer thereof, wherein the deprotecting in steps (A) and (B) comprises deprotection with a Pd/C or Pd(OH)$_2$ catalyst and an acidic ion-exchange resin or an acid, wherein the acid is selected from a group consisting of phosphoric acid, hydrochloric acid, sulfuric acid, methanesulfonic acid, trifluoromethanesulfonic acid, p-toluenesulfonic acid, benzenesulfonic acid, boron trifluoride, and phosphorus oxychloride, (3) reducing the compound having a configuration represented by the formula (XXIV) or the enantiomer thereof in the presence of DIBAL-H, sodium bis-2-methoxyethoxyaluminum hydride, or lithium aluminum tri-t-butoxyhydride to form a compound having a configuration represented by the formula (XXV):

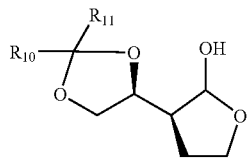

(XXV)

or the enantiomer thereof
wherein $R_{10}$ and $R_{11}$ are as defined above, and (4) deprotecting and cyclizing the compound having a configuration represented by the formula (XXV) or the enantiomer thereof with an acid to form the compound having a configuration represented by the formula (XXVI) or the enantiomer thereof, wherein the acid is selected from a group consisting of hydrochloric acid, sulfuric acid, phosphoric acid, methanesulfonic acid, p-toluenesulfonic acid, and a strong acidic ion-exchange resin.

4. The method of claim 3, wherein $R_{10}$ and $R_{11}$ are the same or different and each is independently a hydrogen atom, a lower alkyl group, a lower alkoxyl group or a phenyl group.

5. The method of claim 3, wherein the method involves
the compound of formula (XXII),
the compound of formula (XXIV),
the compound of formula (XXV), and
the compound of formula (XXVI).

6. The method of claim 3, wherein the stereoselective reduction is an asymmetric hydrogenation reaction using a transition metal catalyst, wherein the transition metal catalyst comprises
(a) an asymmetric ligand which is an optically active phosphine derivative selected from the group consisting of the compounds represented by the following formulas:

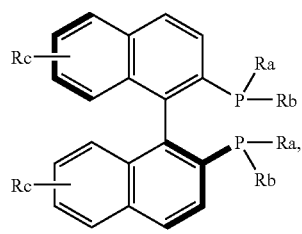

(L1)

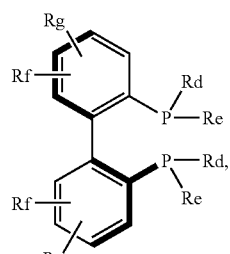

(L2)

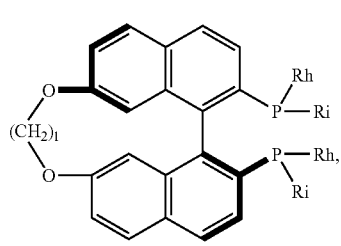

(L3)

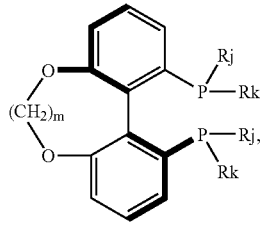

(L4)

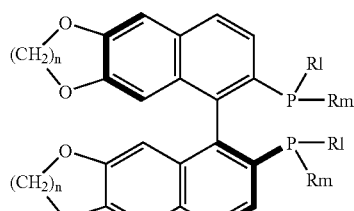

(L5)

and

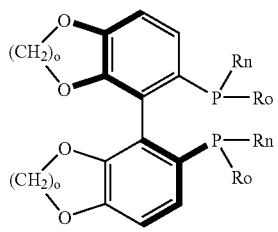

(L6)

wherein Ra, Rb, Rd, Re, Rh, Ri, Rj, Rk, Rl, Rm, Rn and Ro are the same or different and each is independently an optionally substituted phenyl or an optionally substituted cyclohexyl, Rc, Rf and Rg are the same or different and each is independently a hydrogen atom, a halogen atom, alkyl, alkoxy or an optionally substituted phenyl and l, m, n and o are each independently an integer of 1-6, and enantiomers thereof, and (b) ruthenium.

7. The method of claim 6, wherein
the asymmetric ligand is an optically active phosphine derivative selected from the group consisting of the compounds of the formulas (L1), (L2), (L3), (L4), (L5) and (L6), and
the compound having a configuration represented by the formula (XXII) is formed in step (1),
or
the asymmetric ligand is an optically active phosphine derivative selected from the group consisting of enantiomers of the compounds of the formulas (L1), (L2), (L3), (L4), (L5) and (L6), and
the enantiomer of the compound having a configuration represented by the formula (XXII) is formed in step (1).

8. A method for producing a compound having a configuration represented by the formula (XV):

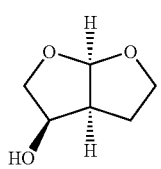

(XV)

or the enantiomer thereof wherein the method comprises
deprotecting and cyclizing a compound having a configuration represented by the formula (XXV):

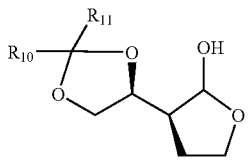

(XXV)

or the enantiomer thereof
wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an α,ω-alkylene group having 2 to 5 carbon atoms, wherein one of the carbon atoms at positions other than α-position and ω-position is optionally substituted by an oxygen atom or a sulfur atom,
with an acid to form a compound having a configuration represented by the formula (XXVI):

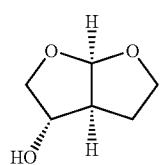

(XXVI)

or the enantiomer thereof
wherein the acid is selected from a group consisting of hydrochloric acid, sulfuric acid, phosphoric acid, methanesulfonic acid, p-toluenesulfonic acid, and a strong acidic ion-exchange resin, and
inverting the hydroxyl group of the compound having a configuration represented by the formula (XXVI) or the enantiomer thereof to form the compound having a configuration represented by the formula (XV) or the enantiomer thereof.

9. The method of claim 8, wherein inverting the hydroxyl group of the compound having a configuration represented by the formula (XXVI) or the enantiomer thereof comprises the following step (2C) or (2D):
(2C) oxidizing the compound having a configuration represented by the formula (XXVI) or the enantiomer thereof in the presence of oxalyl chloride and dimethyl sulfoxide to form a compound having a configuration represented by the formula (XXVII):

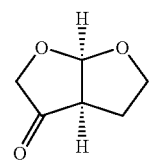

(XXVII)

or the enantiomer thereof, and
reducing the compound having a configuration represented by the formula (XXVII) or the enantiomer thereof in the presence of lithium aluminum hydride, sodium borohydride, lithium borohydride, or DIBAL-H to form the compound having a configuration represented by the formula (XV) or the enantiomer thereof, or
(2D) inversion esterification of the compound having a configuration represented by the formula (XXVI) or the enantiomer thereof in the presence of (i) triphenylphosphine or trialkylphosphine and (ii) azodicarboxylic acid ester or azodicarboxylic amide, to form a compound having a configuration represented by the formula (XXVIII):

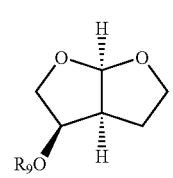

(XXVIII)

or the enantiomer thereof
wherein $R_9$ is an alkanoyl group wherein a hydrogen atom is optionally substituted by a fluorine atom or a chlorine atom, or a benzoyl group wherein a hydrogen atom of a phenyl group is optionally substituted by a nitro group, a halogen, an alkyl group, an alkoxyl group or a phenyl group, and
hydrolyzing the compound having a configuration represented by the formula (XXVIII) or the enantiomer thereof in the presence of a base to form the compound having a configuration represented by the formula (XV) or the enantiomer thereof.

10. The method of claim 8, wherein the method involves
the compound of formula (XXVI), and
the compound of formula (XV).

11. The method of claim 8, wherein $R_{10}$ and $R_{11}$ are the same or different and each is independently a hydrogen atom, a lower alkyl group, a lower alkoxyl group or a phenyl group.

12. The method of claim 8, wherein the compound having a configuration represented by the formula (XXV) or the enantiomer thereof is obtained by
(1) stereoselectively reducing a compound represented by the formula (XXI):

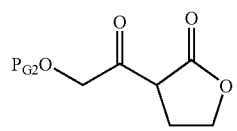

(XXI)

wherein $P_{G2}$ is a hydroxy-protecting group,
to form a compound having a configuration represented by the formula (XXII):

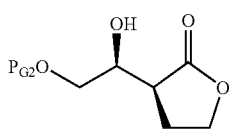

(XXII)

or the enantiomer thereof
wherein $P_{G2}$ is as defined above, (2) using the compound having a configuration represented by the formula (XXII) or the enantiomer thereof in a reaction to form a compound having a configuration represented by the formula (XXIV):

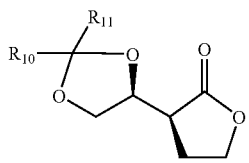
(XXIV)

or the enantiomer thereof
wherein $R_{10}$ and $R_{11}$ are the same or different and each is independently a hydrogen atom, a lower alkyl group, a lower alkoxyl group or a phenyl group, or $R_{10}$ and $R_{11}$ are optionally taken together to form an α,ω-alkylene group having 2 to 5 carbon atoms, wherein one of the carbon atoms at positions other than α-position and ω-position is optionally substituted by an oxygen atom or a sulfur atom,
wherein the reaction comprises the following step (A) or (B):
(A) simultaneously deprotecting the compound having a configuration represented by the formula (XXII) or the enantiomer thereof and introducing a diol protecting group into the compound having a configuration represented by the formula (XXII) or the enantiomer thereof or
(B) deprotecting the compound having a configuration represented by the formula
(XXII) or the enantiomer thereof to form a compound having a configuration represented by the formula (XXIII):

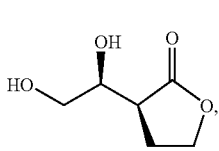
(XXIII)

or the enantiomer thereof, and
introducing a diol protecting group into the compound having a configuration represented by the formula (XXIII) or the enantiomer thereof,
wherein the deprotecting in steps (A) and (B) comprises deprotection with a Pd/C or Pd(OH)$_2$ catalyst and an acidic ion-exchange resin or an acid, wherein the acid is selected from a group consisting of phosphoric acid, hydrochloric acid, sulfuric acid, methanesulfonic acid, trifluoromethanesulfonic acid, p-toluenesulfonic acid, benzenesulfonic acid, boron trifluoride, and phosphorous oxychloride, and
(3) reducing the compound having a configuration represented by the formula (XXIV) or the enantiomer thereof in the presence of DIBAL-H, sodium bis-2-methoxyethoxyaluminum hydride, or lithium aluminum tri-t-butoxyhydride.
13. The method of claim 12, wherein the method involves the compound of formula (XXII),
the compound of formula (XXIV),
the compound of formula (XXV), and
the compound of formula (XXVI).

14. The method of claim 12, wherein the stereoselective reduction is an asymmetric hydrogenation reaction using a transition metal catalyst, wherein the transition metal catalyst comprises
(a) an asymmetric ligand which is an optically active phosphine derivative selected from the group consisting of the compounds represented by the following formulas:

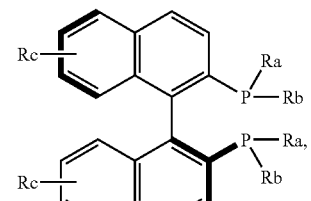
(L1)

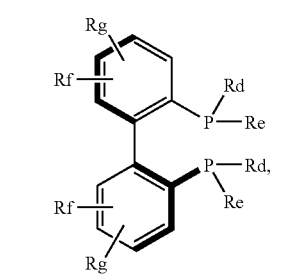
(L2)

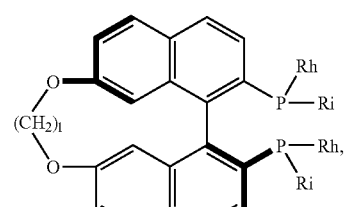
(L3)

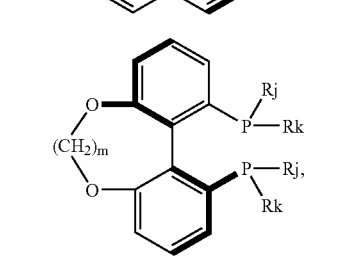
(L4)

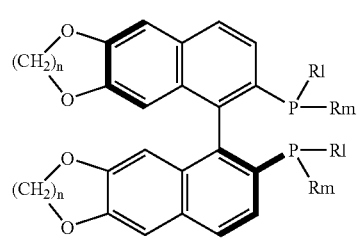
(L5)

and

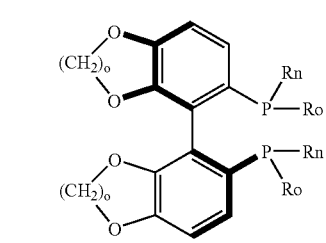
(L6)

wherein Ra, Rb, Rd, Re, Rh, Ri, Rj, Rk, Rl, Rm, Rn and Ro are the same or different and each is independently an optionally substituted phenyl or an optionally substituted cyclohexyl, Rc, Rf and Rg are the same or different and each is independently a hydrogen atom, a halogen atom, alkyl, alkoxy or an optionally substituted phenyl and l, m, n and o are each independently an integer of 1-6, and enantiomers thereof, and (b) ruthenium.

15. The method of claim 14, wherein
the asymmetric ligand is an optically active phosphine derivative selected from the group consisting of the compounds of the formulas (L1), (L2), (L3), (L4), (L5) and (L6), and
the compound having a configuration represented by the formula (XXII) is formed in step (1),
or
the asymmetric ligand is an optically active phosphine derivative selected from the group consisting of enantiomers of the compounds of the formulas (L1), (L2), (L3), (L4), (L5) and (L6), and
the enantiomer of the compound having a configuration represented by the formula (XXII) is formed in step (1).

16. The method of claim 3, wherein the method involves
the enantiomer of the compound of formula (XXII),
the of the compound of formula (XXIV),
the enantiomer of the compound of formula (XXV), and
the enantiomer of the compound of formula (XXVI).

17. The method of claim 8, wherein the method involves
the enantiomer of the compound of formula (XXVI), and
the enantiomer of the compound of formula (XV).

18. The method of claim 12, wherein the method involves
the enantiomer of the compound of formula (XXII),
the enantiomer of the compound of formula (XXIV),
the enantiomer of the compound of formula (XXV), and
the enantiomer of the compound of formula (XXVI).

* * * * *